(12) United States Patent
Muller et al.

(10) Patent No.: US 12,174,163 B2
(45) Date of Patent: Dec. 24, 2024

(54) PETROLEUM COMPOSITION STITCHING USING BOILING CURVES

(71) Applicant: Saudi Arabian Oil Company, Dhahran (SA)

(72) Inventors: Hendrik Muller, Dhahran (SA); Frederick M. Adam, Dhahran (SA); Imran Ahmed Naqvi, Khobar (SA); Radwan Bakor, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 319 days.

(21) Appl. No.: 17/543,591

(22) Filed: Dec. 6, 2021

(65) Prior Publication Data

US 2023/0176018 A1 Jun. 8, 2023

(51) Int. Cl.
*G01N 30/86* (2006.01)
*G01N 30/72* (2006.01)
*G01N 33/28* (2006.01)

(52) U.S. Cl.
CPC ..... *G01N 30/8682* (2013.01); *G01N 30/7206* (2013.01); *G01N 30/8693* (2013.01); *G01N 33/287* (2013.01)

(58) Field of Classification Search
CPC ........... G01N 30/7206; G01N 30/8682; G01N 30/8693; G01N 33/287; G01N 2030/8854; G01N 33/2823
USPC .......................................................... 702/25
See application file for complete search history.

(56) References Cited

U.S. PATENT DOCUMENTS

| 7,556,716 B2 | 7/2009 | Burian et al. |
| 7,820,015 B2 | 10/2010 | Burian et al. |
| 8,682,597 B2 | 3/2014 | Brown et al. |
| 9,665,693 B2 * | 5/2017 | Saeger ................. G16C 10/00 |
| 2007/0050154 A1 | 3/2007 | Tareq |

(Continued)

OTHER PUBLICATIONS

U.S. Appl. No. 17/356,142, Muller, filed Jun. 23, 2021.

(Continued)

*Primary Examiner* — Yoshihisa Ishizuka
*Assistant Examiner* — Joshua L Forristall
(74) *Attorney, Agent, or Firm* — Fish & Richardson P.C.

(57) ABSTRACT

Systems and methods include a computer-implemented method for analyzing petroleum samples. Different boiling curves are received that are calculated for a petroleum sample using different analytical speciation techniques. The boiling curves include: 1) a detailed hydrocarbon analysis (DHA) is used for a speciation of light-end components of the petroleum sample; 2) a comprehensive 2-dimensional (2D) gas chromatography (GCxGC) is used for a speciation of a middle distillates range of the petroleum sample; and 3) a high-resolution mass spectrometry is used for a speciation of heavy-end components of the petroleum sample. A compositional coverage of the different analytical speciation techniques for the petroleum samples is determined using the different boiling curves. Each of the different analytical speciation techniques covers a different boiling range and produces a compositional model modeling a breakdown of components in the petroleum sample by carbon number, aromatic ring family, and heteroatom class.

20 Claims, 26 Drawing Sheets

(56) References Cited

U.S. PATENT DOCUMENTS

| | | | |
|---|---|---|---|
| 2007/0114377 A1* | 5/2007 | Qian | G01N 33/28 250/282 |
| 2009/0059995 A1 | 3/2009 | Burian et al. | |
| 2010/0204925 A1 | 8/2010 | Albahri | |
| 2014/0107941 A1* | 4/2014 | Albahri | G01N 33/0004 702/24 |
| 2018/0143168 A1* | 5/2018 | Wang | G01N 30/6034 |

OTHER PUBLICATIONS

Adam et al., "Supercritical fluid chromatography hyphenated with twin comprehensive two-dimensional gas chromatography for ultimate analysis of middle distillates," Journal of Chromatography A, 2010, 1217:1386-139, 9 pages.

Alawani et al., "Characterization of Crude Oils through Alkyl Chain-Based Separation by Gel Permeation Chromatography and Mass Spectrometry," Energy Fuels, 2020, 34(5):5414-5425, 38 pages.

Beckey et al., "Field desorption mass spectrometry: A technique for the study of thermally unstable substances of low volatility," Ion Phys. Journal of Mass Spectrometry and Ion Physics, 1969, 2:500-503, 3 pages.

Behrenbruch et al., "Classification and characterisation of crude oils based on distillation properties," Journal of Petroleum Science and Engineering 2007, 57(1-2):166-180, 15 pages.

Djokic et al., "Combined characterization using HT-GCxGC-FID and FT-ICR MS: A pyrolysis fuel oil case study," Fuel Processing Technology 2018, 182, 15-25, 11 pages.

França et al., "Speciation and quantification of high molecular weight paraffins in Brazilian whole crude oils using high-temperature comprehensive two-dimensional gas chromatography," Fuel, 2018, 234:1154-1164, 11 pages.

Gross et al., "Field desorption mass spectrometry of large multiply branched saturated Hydrocarbons," Journal of Mass Spectrometry 2001, 36:522-528, 7 pages.

Hodgkins et al., "Hydrodearylation of Heavy Alkyl-Bridged Noncondensed Alkyl Aromatics to Recover High-Value Mono-Aromatics," Industrial & Engineering Chemistry Research, 2019, 58:19042-19049, 31 pages.

Kinney, "A system correlating molecular structure of organic compounds with their boiling points," J. Org. Chem., 1941, 6:220-228, 9 pages.

Kinney, "A system correlating molecular structure of organic compounds with their boiling points, " J. Am. Chem. Soc., 1938, 60:3032-3039, 8 pages.

Kinney, "Calculation of Boiling Points of Aliphatic Hydrocarbons," Ind. Eng. Chem. 1940, 32(4):559-562, 4 pages.

Kudchadker et al., "Vapor Pressure and Boiling Points of Normal Alkanes, $C_{21}$ to $C_{100}$," Journal of Chemical and Engineering Data, 1966, 11(2):253-255, 3 pages.

Kumar et al., "Mechanistic Kinetic Modeling of the Hydrocracking of Complex Feedstocks, such as Vacuum Gas Oils," Industrial & Engineering Chemistry Research, 2007, 46(18):5881-5897, 17 pages.

Li et al., "Quantitative molecular composition of heavy petroleum fractions: a case study of fcc decant oil," Energy & Fuels, 2020, 26 pages.

Li et al., "Selective methylation of sulfides in petroleum for electrospray ionization mass spectrometry analysis," Energy & Fuels, 2019, 33:1797-1802, 6 pages.

Lopes et al., "Extending the true boiling point curve of a heavy crude oil by means of molecular distillation and characterization of the products obtained," Petroleum Science and Technology, 2017, 35(14):1523-1529, 8 pages.

Lozano et al., "Pushing the analytical limits: new insights into complex mixtures using mass spectra segments of constant ultrahigh resolving power," Chemical Science, 2019, 10, 14 pages.

Mahé et al., "Overcoming the high-temperature two-dimensional gas chromatography limits to elute heavy compounds, " Journal of Chromatography A, 2012, 1229:298-301, 4 pages.

Marshall et al., "Petroleomics: Chemistry of the underworld," Proceedings of the National Academy of Sciences PNAS, 2008, 105(47):18093-18095, 6 pages.

Mennito et al., "Characterization of Heavy Petroleum Saturates by Laser Desorption Silver Cationization and Fourier Transform Ion Cyclotron Resonance Mass Spectrometry," Energy Fuels, 2013, 27(12):7348-7353, 6 pages.

Miquel et al., "A new method for petroleum fractions and crude oil characterization," SPE Reservoir Engineering, May 1992, 7(2):265-270, 6 pages.

Müller et al., "Characterization of high-molecular-weight sulfur-containing aromatics in vacuum residues using Fourier transform ion cyclotron resonance mass spectrometry," Analytical Chemistry, 2005, 77(8):2536-2543, 8 pages.

Muller et al., "Evaluation of Quantitative Sulfur Speciation in Gas Oils by Fourier Transform Ion Cyclotron Resonance Mass Spectrometry: Validation by Comprehensive Two-Dimensional Gas Chromatography," Journal American Society Mass Spectrometry, 2012, 23:806-815, 10 pages.

Muller et al., "Innate Sulfur Compounds as an Internal Standard for Determining Vacuum Gas Oil Compositions by APPI FT-ICR MS," Energy Fuels, Jun. 2020, 34:8260-8273, 52 pages.

Muller et al., "Narrow Distillation Cuts for an Improved Characterization of Crude Oil: An Insight on Heteroatoms in Heavy Fraction Molecules," International J. Oil, Gas and Coal Technology, 2021, 26(1):40-59, 20 pages.

Muller et al., "Saturated Compounds in Heavy Petroleum Fractions," Energy & Fuels, 2020, 35 pages.

Ng et al., "Distributions of Aromatics, Nitrogen, and Sulfur in Cracked Liquid Products from Microactivity Tests," Energy & Fuels, 2000, 14(4): 945-946, 2 pages.

Potgieter et al., "Analysis of oxidised heavy paraffininc products by high temperature comprehensive two-dimensional gas chromatography," J Chromatogr A, 2017, 1509:123-131, 9 pages.

Purcell et al., "Atmospheric Pressure Photoionization Fourier Transform Ion Cyclotron Resonance Mass Spectrometry for Complex Mixture Analysis," Analytical Chemistry, 2006, 78(16):5906-5912, 7 pages.

Qian et al., "Characterization of large nonvolatile polyaromatic molecules by a combination of in-source pyrolysis and field desorption mass spectrometry," Energy Fuels, 2001, 15(4):949-954, 6 pages.

Qian et al., "Desorption and Ionization of Heavy Petroleum Molecules and Measurement of Molecular Weight Distributions," Energy Fuels, 2007, 21:1042-1047, 6 pages.

Qian et al., "Resolution and Identification of Elemental Compositions for More than 3000 Crude Acids in Heavy Petroleum by Negative-Ion Microelectrospray High Field Fourier Transform Ion Cyclotron Resonance Mass Spectrometry," Energy & Fuels, 2001, 15(6):1505-1511, 7 pages.

Reiter et al., "Characterization of crude oil by real component surrogates," Energy & Fuels, 2014, 28(8):5565-5571, 7 pages.

Revellin et al., "Specific Nitrogen Boiling Point Profiles of Vacuum Gasoils," Energy & Fuels, 2005, 19(6):2438-2444, 7 pages.

Rodgers et al., "Molecular Characterization of Petroporphyrins in Crude Oil by Electrospray Ionization Fourier Transform Ion Cyclotron Resonance Mass Spectrometry," Canadian Journal of Chemistry, 2001, 79:546-551, 6 pages.

Rodgers et al., "Petroleum Analysis," Analytical Chemistry, 2011, 83:4665-4687, 23 pages.

Shearer et al., "Simultaneous measurement of hydrocarbons and sulfur compounds using flame ionization and sulfur chemiluminescence detection for sulfur simulated distillation," Journal of High Resolution Chromatography, 1999, 22(7):386-390, 5 pages.

Vendeuvre et al., "Characterisation of middle-distillates by comprehensive two-dimensional gas chromatography (GC x GC): A powerful alternative for performing various standard analysis of middle-distillates," Journal of chromatography A, 2005, 1086(1-2):21-28, 8 pages.

(56) References Cited

OTHER PUBLICATIONS

Wang et al., "Detailed Chemical Composition of Straight-Run Vacuum Gas Oil and its Distillates as a Function of the Atmospheric Equivalent Boiling Point," Energy Fuels, 2016, 30(2):968-974, 7 pages.
Xavier et al., "On the use of continuous distribution models for characterization of crude oils," Latin American Applied Research, 2011, 41(4):325-329, 5 pages.
Zhou et al., "Characterization of Saturated Hydrocarbons in Vacuum Petroleum Residua: Redox Derivatization Followed by Negative-Ion Electrospray Ionization Fourier Transform Ion Cyclotron Resonance Mass Spectrometry," Energy Fuels, 2014, 28(1):417-422, 6 pages.

* cited by examiner

208

| NR | AR | C | DBE | FID | AEBP |
|---|---|---|---|---|---|
| 0 | 0 | 6 | 0 | 0.00% | 63.4 |
| 0 | 0 | 7 | 0 | 0.00% | 99.8 |
| 0 | 0 | 8 | 0 | 0.00% | 131.4 |
| 0 | 0 | 9 | 0 | 0.02% | 159.2 |
| 0 | 0 | 10 | 0 | 0.08% | 184.1 |
| 0 | 0 | 11 | 0 | 0.13% | 206.7 |
| 0 | 0 | 12 | 0 | 0.18% | 227.2 |
| 0 | 0 | 13 | 0 | 0.29% | 246.2 |
| 0 | 0 | 14 | 0 | 0.83% | 263.7 |
| 0 | 0 | 15 | 0 | 1.10% | 280.0 |
| 0 | 0 | 16 | 0 | 1.32% | 295.3 |
| 0 | 0 | 17 | 0 | 1.45% | 309.6 |
| 0 | 0 | 18 | 0 | 1.60% | 323.1 |
| 0 | 0 | 19 | 0 | 1.37% | 335.9 |
| 0 | 0 | 20 | 0 | 1.39% | 348.0 |
| 0 | 0 | 21 | 0 | 1.28% | 359.6 |
| 0 | 0 | 22 | 0 | 0.98% | 370.6 |
| 1 | 0 | 9 | 1 | 0.00% | 166.7 |
| 1 | 0 | 10 | 1 | 0.03% | 191.7 |
| 1 | 0 | 11 | 1 | 0.06% | 214.2 |
| 1 | 0 | 12 | 1 | 0.09% | 234.8 |
| 1 | 0 | 13 | 1 | 0.19% | 253.7 |
| 1 | 0 | 14 | 1 | 0.29% | 271.2 |
| 1 | 0 | 15 | 1 | 0.48% | 287.5 |
| 1 | 0 | 16 | 1 | 0.76% | 302.8 |
| 1 | 0 | 17 | 1 | 0.69% | 317.1 |
| 1 | 0 | 18 | 1 | 0.59% | 330.6 |
| 1 | 0 | 19 | 1 | 0.76% | 343.4 |
| 1 | 0 | 20 | 1 | 0.47% | 355.5 |
| 1 | 0 | 21 | 1 | 0.60% | 367.1 |
| 1 | 0 | 22 | 1 | 0.55% | 378.1 |
| 2 | 0 | 10 | 2 | 0.00% | 197.7 |
| 2 | 0 | 11 | 2 | 0.02% | 220.2 |
| 2 | 0 | 12 | 2 | 0.05% | 240.8 |
| 2 | 0 | 13 | 2 | 0.04% | 259.7 |
| 2 | 0 | 14 | 2 | 0.09% | 277.2 |
| 0 | 1 | 6 | 4 | 0.00% | 84.4 |
| 0 | 1 | 7 | 4 | 0.01% | 120.9 |
| 0 | 1 | 8 | 4 | 0.07% | 152.4 |
| 0 | 1 | 9 | 4 | 0.87% | 180.3 |
| 0 | 1 | 10 | 4 | 0.98% | 205.2 |
| 0 | 1 | 11 | 4 | 1.16% | 227.7 |
| 0 | 1 | 12 | 4 | 0.52% | 248.3 | continued..

210

| AEBP | CUMULATIVE |
|---|---|
| 63.4 | 0.00% |
| 84.4 | 0.00% |
| 99.8 | 0.00% |
| 120.9 | 0.01% |
| 131.4 | 0.01% |
| 152.4 | 0.08% |
| 159.2 | 0.10% |
| 166.7 | 0.10% |
| 180.3 | 0.97% |
| 181.8 | 1.07% |
| 181.8 | 1.07% |
| 184.1 | 1.15% |
| 191.7 | 1.18% |
| 197.7 | 1.19% |
| 205.2 | 2.17% |
| 205.2 | 2.98% |
| 206.7 | 3.10% |
| 206.7 | 3.74% |
| 206.7 | 3.92% |
| 214.2 | 3.98% |
| 220.2 | 4.00% |
| 227.2 | 4.18% |
| 227.7 | 5.34% |
| 227.8 | 10.37% |
| 229.2 | 11.28% |
| 229.3 | 11.64% |
| 234.8 | 11.73% |
| 240.8 | 11.78% |
| 240.8 | 12.18% |
| 245.3 | 12.75% |
| 246.2 | 13.04% |
| 248.3 | 13.56% |
| 248.3 | 25.36% |
| 249.8 | 26.94% |
| 249.8 | 27.14% |
| 253.7 | 27.33% |
| 259.7 | 27.37% |
| 259.8 | 28.61% |
| 263.7 | 29.44% |
| 264.3 | 32.25% |
| 267.2 | 32.87% |
| 267.3 | 42.54% |
| 268.7 | 43.71% | continued..

FIG. 2B

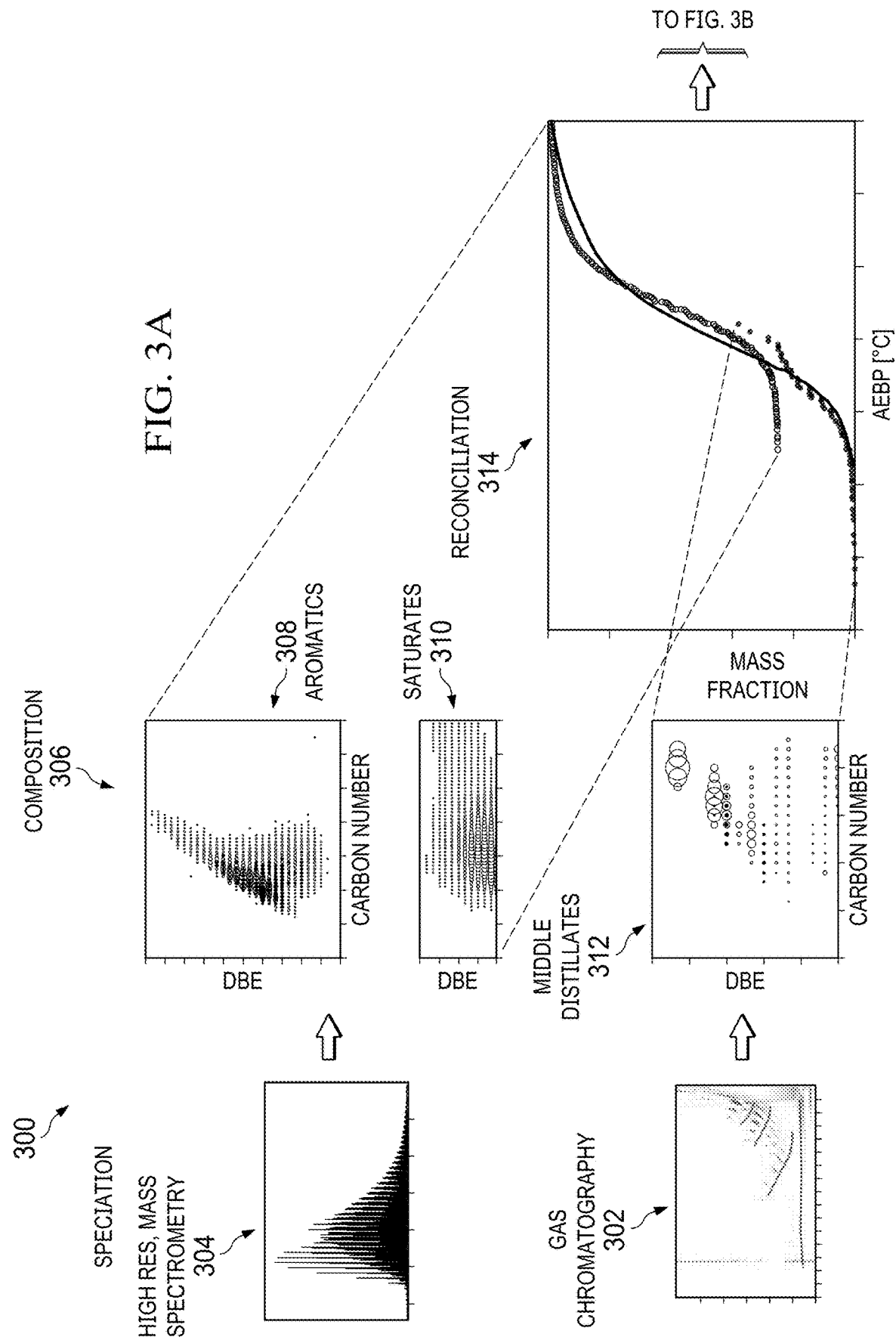

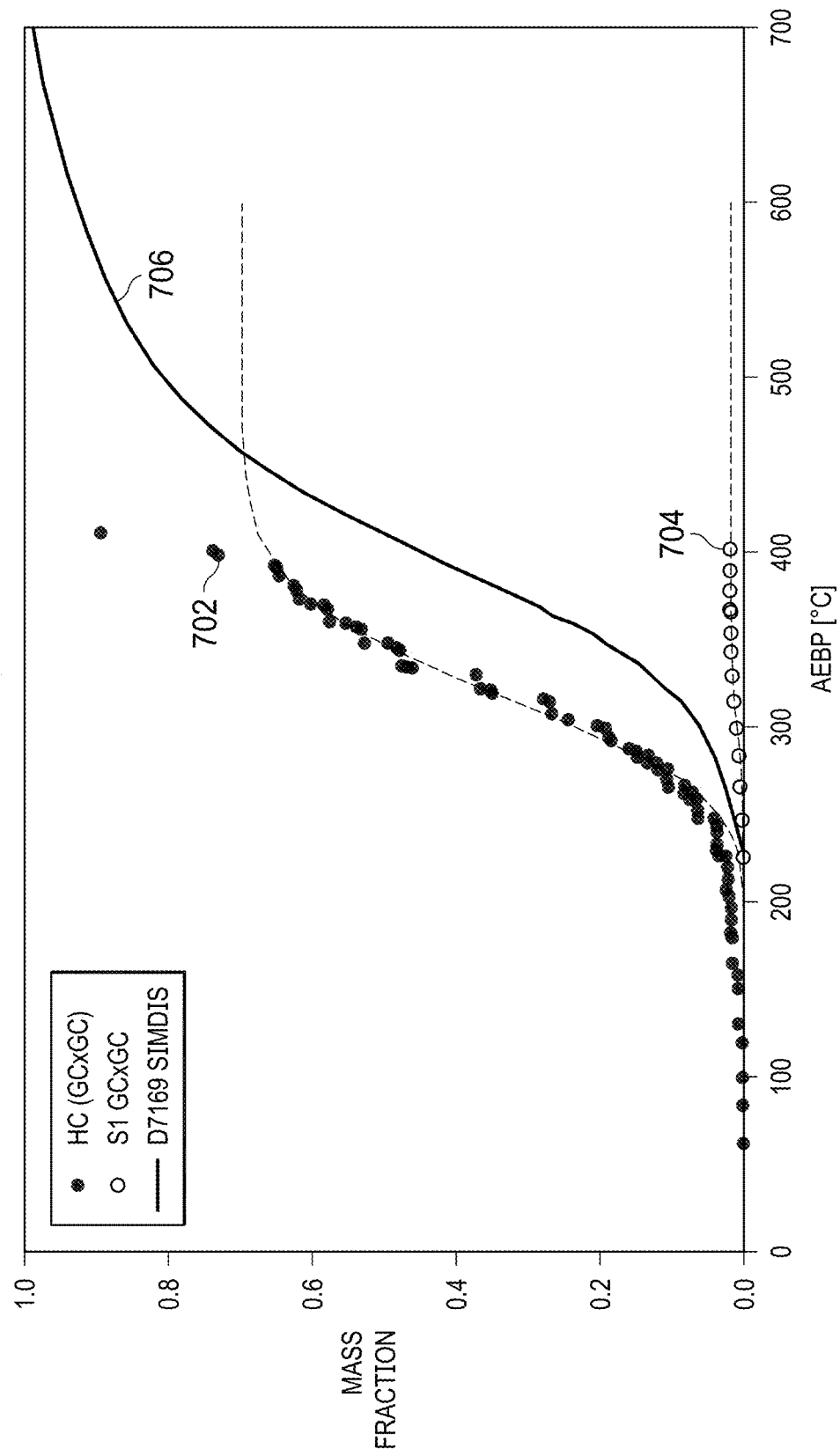

PETROLEUM COMPOSITION STITCHING USING BOILING CURVES

TECHNICAL FIELD

The present disclosure applies to determining properties of petroleum products, such as crude oil.

BACKGROUND

The development of hydrocarbon conversion technologies requires chemical information of feedstocks, intermediates, and products. More detailed and accurate chemical information improves the process of determining conversion parameters, evaluating process steps, and allows technology optimization. In the case of processes that target petroleum streams with a wide boiling range, such as processes that aim at whole crude oil upgrading or residue conversion, a number of complementary analytical techniques are required to obtain a meaningful chemical description of the sample. Multiple techniques are required because each technique has limitations in regards to its accessible boiling range. For example, for large-scale processes, physical distillation of feedstock and product streams can be used to prepare sub-fractions suitable for individual analyses. However, conversion experiments during early project stages may yield very little product volume, which in most cases prevents quantitative physical fractionation. The small product volume is therefore a limiting factor for the available product characterization, as advanced speciation techniques cannot be presently applied quantitatively to an unfractionated sample.

Petroleum and its fractions are extremely complex mixtures of hundreds of thousands, or millions of different molecules. While the bulk characterization (average properties and approximate chemical composition) is known, the development and optimization of oil and gas technologies benefits immensely from knowing the feedstocks, intermediates, and products, and therefore the chemical transformation of those streams, at the level of individual molecules. Such detailed knowledge enables "molecular refining" with technologies tailored to the exact chemical composition of the feedstock and product slates.

The molecular characterization of petroleum streams relies on advanced analytical techniques, in particular gas chromatography, comprehensive two-dimensional gas chromatography, and high-resolution mass spectrometry. While these techniques have experienced significant development over the last two decades, each technique has its own limitations in terms of the part of the sample being accessible. For example, gas chromatography is limited by the boiling point of the sample components, high boiling, and non-boiling. Further, "heavy" components cannot be analyzed. Mass spectrometric methods are able to access the heavy components, but the methods ignore the smaller (or "lighter") boiling molecules. Mass spectrometry also requires ionization of the sample constituents, which is not universally available for all compound classes. As a result, multiple methods of ionization need to be applied, depending on the compounds of interest. Consequentially, a number of different techniques must be used to describe most petroleum samples comprehensively. This situation is further complicated by the fact that it is often unclear how much of the sample has been detected, and how much has been omitted by any technique.

SUMMARY

The present disclosure describes techniques that can be used to determine the chemical composition of petroleum products, such as crude oil. In some implementations, a computer-implemented method includes the following. Different boiling curves are received that are calculated for a petroleum sample using different analytical speciation techniques. The boiling curves include: 1) a detailed hydrocarbon analysis (DHA) is used for a speciation of light-end components of the petroleum sample; 2) a comprehensive 2-dimensional (2D) gas chromatography (GCxGC) is used for a speciation of a middle distillates range of the petroleum sample; and 3) a high-resolution mass spectrometry is used for a speciation of heavy-end components of the petroleum sample. A compositional coverage of the different analytical speciation techniques for the petroleum samples is determined using the different boiling curves. Each of the different analytical speciation techniques covers a different boiling range and produces a compositional model modeling a breakdown of components in the petroleum sample by carbon number, aromatic ring family, and heteroatom class.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. Improvements can be made over conventional paraffin boiling models and petroleum boiling models that are not based on the measurable information obtained using analytical methods. For example, the models do not account for sulfur atoms or the presence of many aromatic rings in conjunction with long alkyl chains in a given modeled compound. Two-dimensional (2D) gas chromatography (GCxGC)-based approaches may use gas chromatographic retention time for obtaining the boiling point of a sample component. This type of approach is limited to GCxGC amenable compounds and requires the availability of standard compounds to correct for chemical structure dependent factors influencing the retention time independently of the boiling point (many standards, for instance highly alkylated aromatic compounds, are not available). Techniques of the present disclosure can provide an improved quantitative boiling point model used to predict boiling curves from comprehensive compositional data obtained using mass spectrometry or GCxGC. The empirical model can be validated against average compositional information for aromatic hydrocarbon, sulfur, and disulfur compounds. The average compositional information may be obtained for narrow boiling range cuts with atmospheric pressure photo ionization (APPI) Fourier-transform ion cyclotron resonance (FTICR) mass spectrometry (MS), field desorption mass spectrometry measurements of isolated saturated compound fractions, and comprehensive 2D gas chromatography measurements. Techniques can be applied to samples that exceed the boiling range of the method without physical fractionation of the sample by distillation. Multiple data sets obtained using different speciation techniques can be combined. Quantitative speciation of small sample quantities is enabled through the elimination of a physical fractionation by distillation. Without this ability, the distillation step requires a certain amount of the sample. Practically, several dozen milliliters of sample may need to be available to achieve a comparable, quantitative distillation. This improvement is essential to produce a molecular speciation for micro-reactor products where sample quantity has been the limiting factor.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIGS. 2A-2C are diagrams collectively showing an example of atmospheric equivalent boiling point (AEBP) curve generation, according to some implementations of the present disclosure.

FIGS. 3A-3B collectively show a schematic overview of an example modeling workflow, according to some implementations of the present disclosure.

FIG. 7 is a graph showing an example of AEBP curves calculated based on the GCxGC based composition model, according to some implementations of the present disclosure.

Like reference numbers and designations in the various drawings indicate like elements.

DETAILED DESCRIPTION

Figure 1:
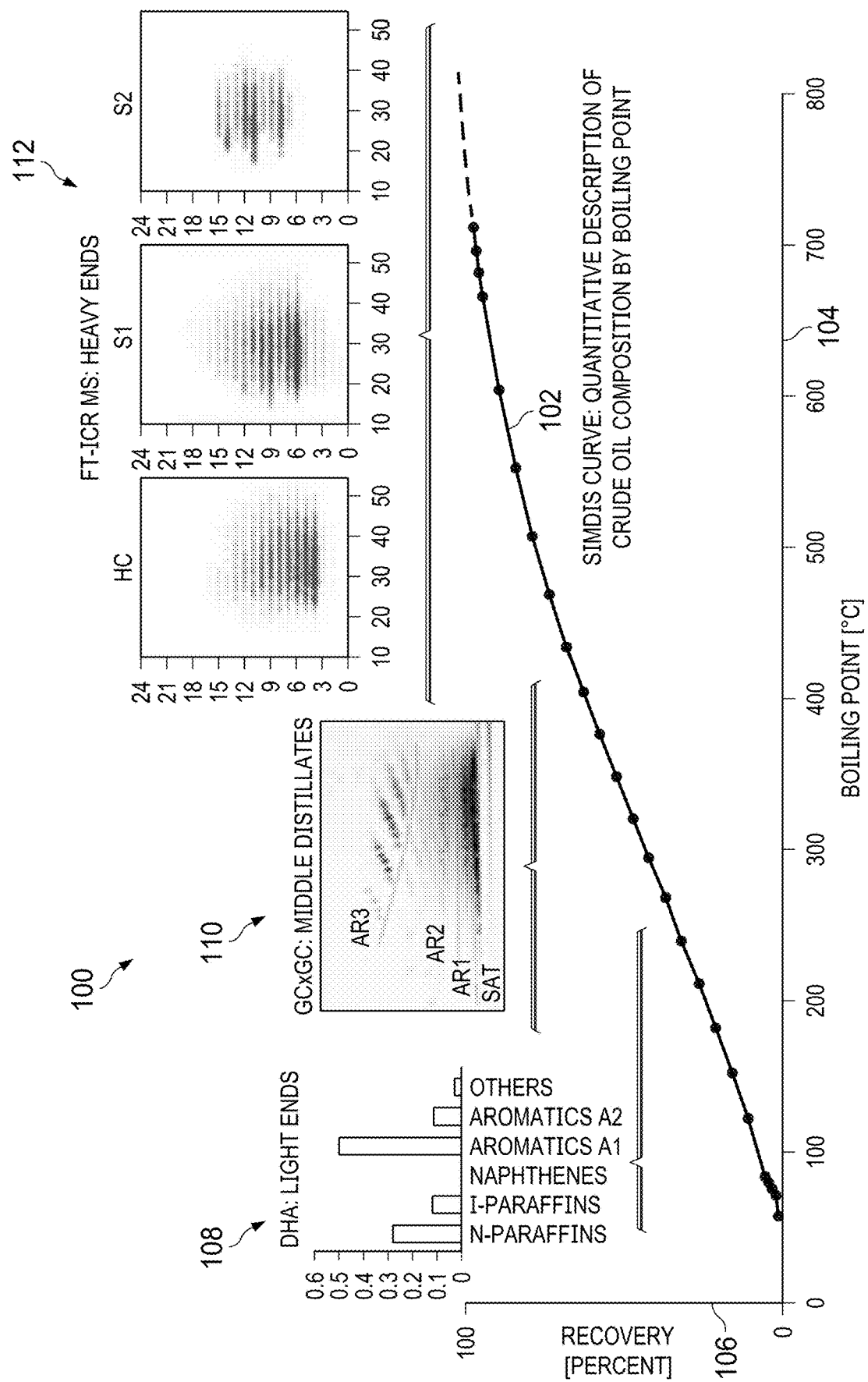
FIG. 1 is a diagram illustrating an example of a concept of crude oil speciation by three methods covering the entire boiling range, according to some implementations of the present disclosure.

The following detailed description describes techniques for determining the chemical composition of petroleum products, such as crude oil. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

To overcome limitations in conventional systems for determining chemical information of feedstocks, intermediates, and products, a quantitative boiling evolution of sample components, based on the individual identified species, can be used for stitching different data sets together quantitatively. For example, stitching together data sets from different analytical techniques, such as gas chromatography, two-dimensional gas chromatography, and high-resolution mass spectrometry is required to obtain a continuous quantitative compositional description. A previously disclosed model allows producing a detailed boiling distribution from molecular parameters determined using state-of-the-art analytical techniques.

In some implementations, a computer-implemented method is used for quantifying, using calculated boiling curves, the compositional coverage of analytical speciation techniques for petroleum samples, where the analytical techniques produce a composition model composed of a breakdown of the sample components by carbon number, aromatic ring family, and heteroatom class. The analytical techniques can cover any boiling range, for instance, but not limited to: 1) detailed hydrocarbon analysis (DHA) for the speciation of light-end components of the petroleum sample; 2) comprehensive 2-dimensional (2D) gas chromatography (GCxGC) for the speciation of a middle distillates range of the petroleum sample; and 3) high-resolution mass spectrometry for the speciation of heavy-end components of the petroleum sample. The compositional model can be normalized and shifted to match the boiling curve of the sample as determined, for instance, by true boiling point distillation or simulated distillation.

In some implementations, a computer-implemented method for quantitatively merging, using calculated boiling curves, the composition models of the sample obtained by a combination of analytical techniques, where the analytical techniques can be any combination covering the sample's boiling range: 1) detailed hydrocarbon analysis (DHA) for the speciation of light-end components of the petroleum sample; 2) comprehensive 2-dimensional (2D) gas chromatography (GCxGC) for the speciation of a middle distillates range of the petroleum sample; and 3) high-resolution mass spectrometry for the speciation of heavy-end components of the petroleum sample. Generating the merged compositional model can include providing, when multiple composition models are quantitatively stitching together, a smooth boiling curve transition between them.

The disclosed method connects such different data sets into one seamless unified composition model, which is furthermore reconciled (e.g., smoothed between the methods) using the routinely available boiling curve by simulated distillation according to international standard methods. The present disclosure opens new quantitation pathways for a micro crude assay that provides the detailed composition for full-range crude oil samples at a very small sample volume (e.g., 1 milliliter (mL)). The developed method overcomes the sample volume requirement that has been a limiting factor for detailed quantitative speciation for hydrocarbon conversion samples in early technology development stages.

The present disclosure describes a method for determining the coverage of advanced speciation techniques (e.g., detailed hydrocarbon analysis, 2D gas chromatography, and high-resolution mass spectrometry) for petroleum samples, and then quantitatively combining speciation data of these different techniques into a comprehensive model of composition using the simulated distillation (SIMDIS) profile of the sample. The concept of different speciation techniques covering different overlapping sections of the samples boiling range is shown in FIG. 1.

To achieve the unified description of the sample composition, the sample's boiling curve is determined using simulated distillation (SIMDIS). State-of-the-art speciation techniques, including, but not limited to, detailed hydrocarbon analysis, 2D gas chromatography, field desorption time-of-flight mass spectrometry and atmospheric pressure photo ionization ion cyclotron resonance mass spectrometry, are applied to the sample, whereby each technique covers detailed speciation of a limited, and unknown portion of the sample. A compositional model is built for each individual technique's data set. The atmospheric equivalent boiling point (AEBP) is calculated for each molecular parameter of each technique's data set. For each data set, the speciated compounds together represent the cumulative boiling curve of the portion of the sample covered by the respective speciation technique. The concept of AEBP curve generation is shown in FIGS. 2A-2C from 2D gas chromatography data.

Finally, the combination of composition models by their respective contribution to the total boiling curve, as determined by simulated distillation (SIMDIS) is used to produce the unified compositional description of the entire sample. The concept of deriving individual models of composition for each speciation technique, obtaining the individual boiling curves, and combining the individual boiling curves is shown in FIGS. 3A-3B.

FIG. 1 is a diagram illustrating an example of a concept 100 of crude oil composition by boiling point, according to some implementations of the present disclosure. A SIMDIS curve 102 covers the boiling range of the sample, plotted relative to a boiling point 104 and a recovery percentage 106. Light ends components 108 are speciated without separation by detailed hydrocarbon analysis (DHA). Middle distillates range 110 is speciated by comprehensive 2D gas chromatography (GCxGC). Heavy ends components 112 are speciated using high-resolution mass spectrometry, for instance Fourier transform ion cyclotron resonance mass spectrometry (FT-ICR MS). Together, the speciation techniques cover the entire sample boiling range, and the different speciation results are combined into a comprehensive description of the sample using the SIMDIS boiling curve 102 and a speciation based boiling model.

Figure 2A:
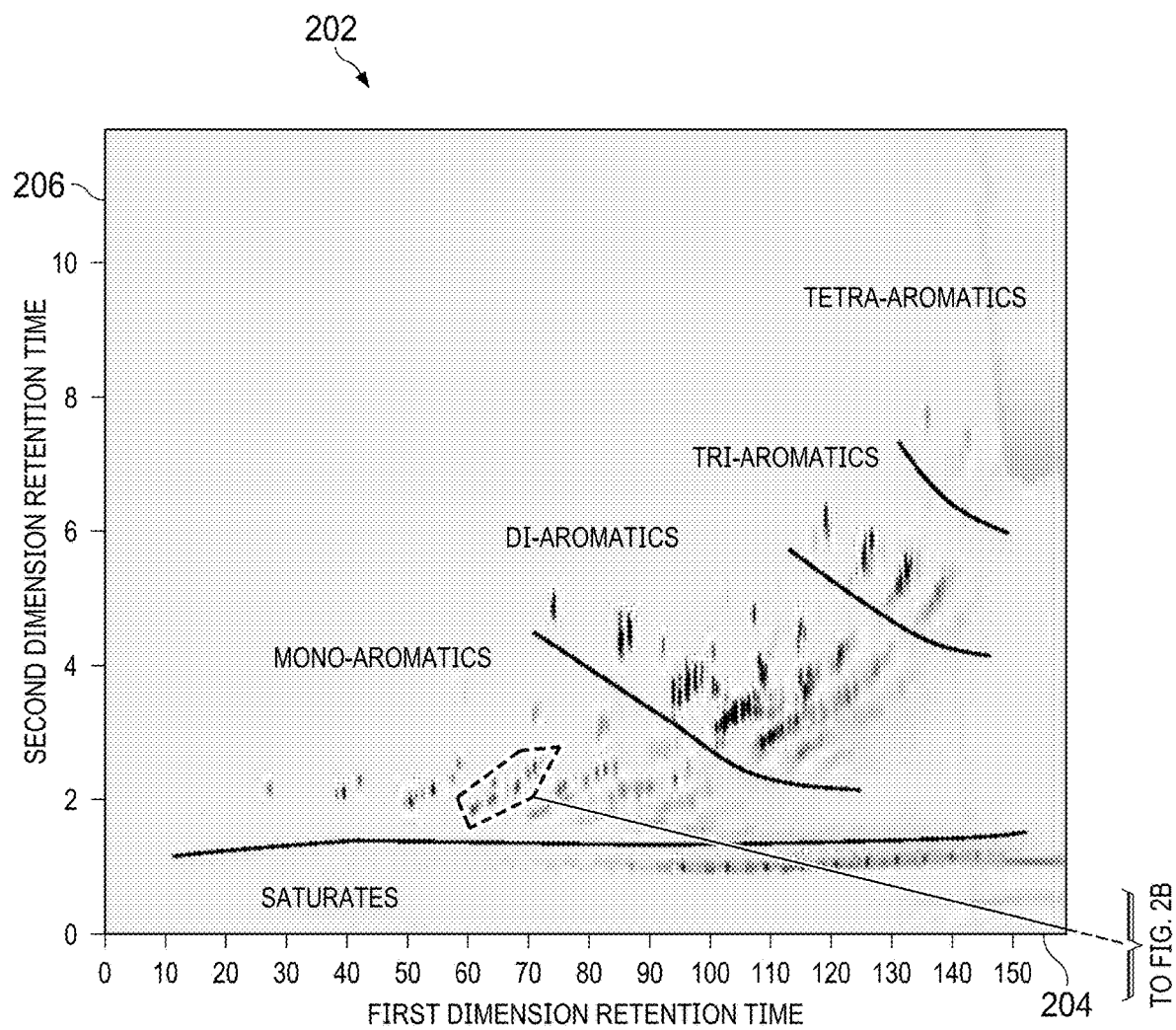
Figure 2C:
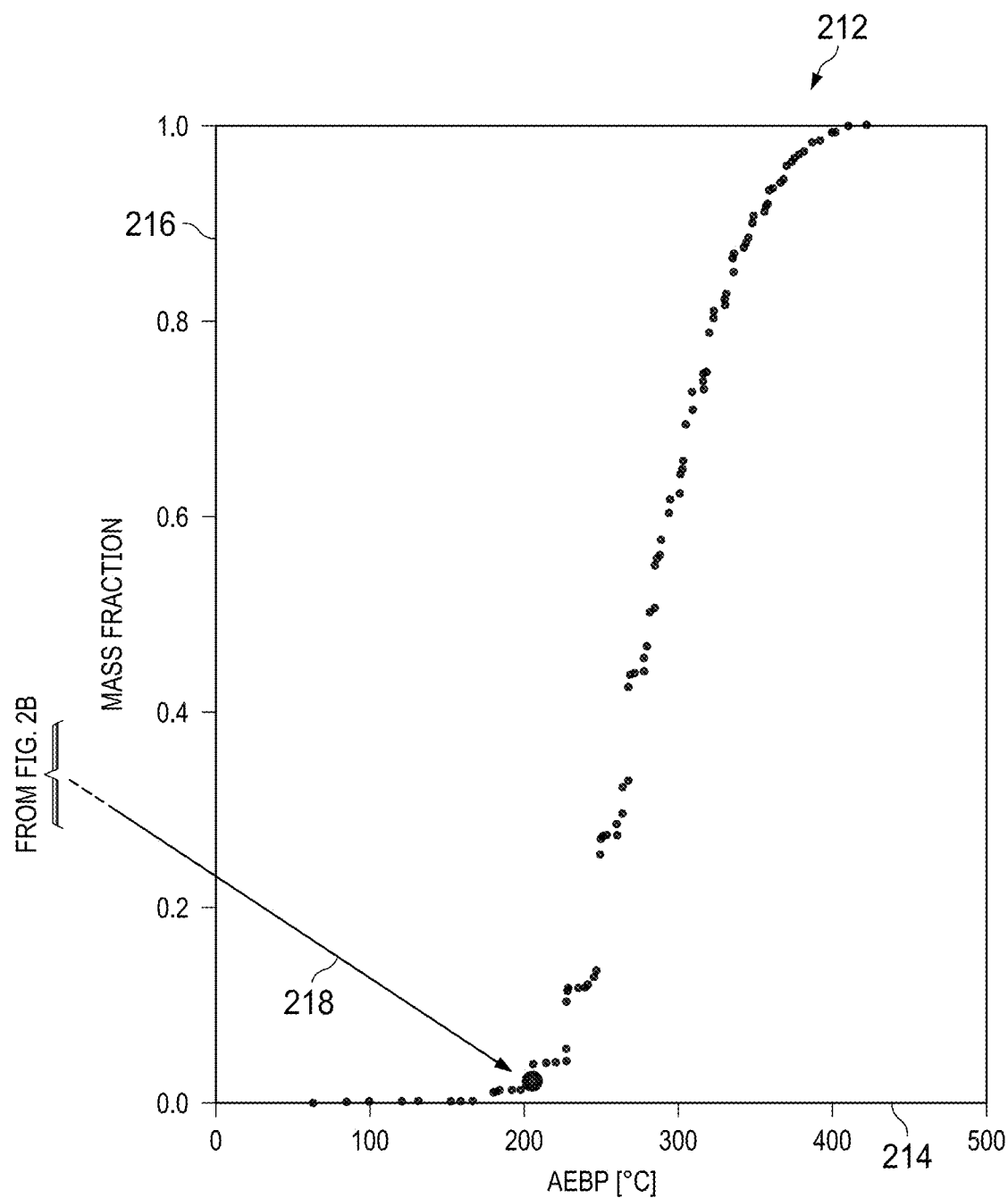

FIGS. 2A-2C are diagrams collectively showing an example of atmospheric equivalent boiling point (AEBP) curve generation, according to some implementations of the present disclosure. Referring to FIG. 2A, a GCxGC flame ionization detector (FID) 2D chromatogram 202 is plotted relative to a first dimension retention time 204 and a second dimension retention time 206. Referring to FIG. 2B, a list of identified components 208 is grouped by C #, DBE, and hetero atoms. AEBP values are calculated for each component. A cumulative mass fraction 210 is sorted by components' AEBP Referring to FIG. 2C, a boiling curve 212 represents the GCxGC-FID data, plotted relative to an AEBP 214 (e.g., in degrees Celsius (° C.)) and a mass fraction 216. It is important to note that the boiling curve represents the underlying composition data in its entirety, including breakdown by carbon number, DBE, and heteroatom class. Markings 218 provide a mapping between selected entries in the AEBP curve generation of FIGS. 2A-2C.

Figure 3B:
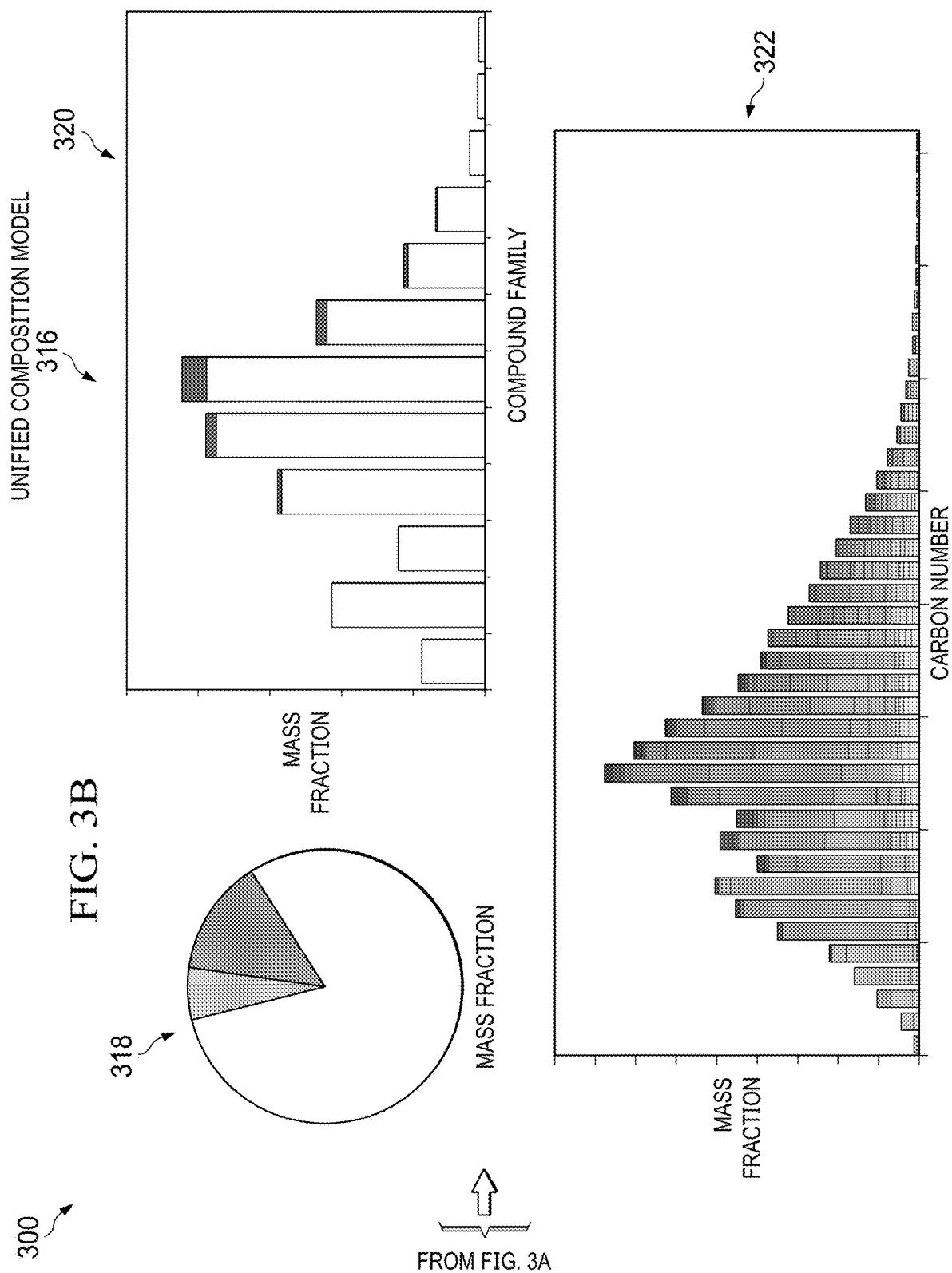

FIGS. 3A-3B collectively show a schematic overview of an example workflow 300 of modeling, according to some implementations of the present disclosure. State-of-the-art characterization data sets (in this example obtained by 2D gas chromatography 302 and high-resolution mass spectrometry 304, are translated into separate models of composition 306 plotted relative to an AEBP (e.g., in ° C.) and a mass fraction. The composition 306 includes aromatics 308, saturates 310, and middle distillates 312. In a reconciliation step 314, the AEBP is calculated for each molecular parameter of the composition models, which together represent the cumulative boiling curve of the portion of the sample covered by the speciation technique. A combination of composition models by their contribution to the total boiling curve determined by simulated distillation (SIMDIS) produces a unified composition model 316 of the entire sample. The model includes a mass fraction pie chart 318, a compound family mass faction graph 320 (see FIG. 16), and a carbon number mass fraction graph 322 (see FIG. 17).

Analytical Methods for Detailed Speciation

For low boiling fractions, that is light ends, quantitative knowledge of the composition has been available for decades through gas chromatography (GC)-based detailed hydrocarbon analysis (DHA). The quantitative knowledge of the individual components can be translated into boiling curves through commercial software tools. The composition of lighter components from C1 to C9 in mass % can be determined by applying the back-flush GC-FID technique. The components C9+ can be vented through the back-flush valve. The simulated distillation by GC-FID can be used to determine the boiling range from C5 to C100 in crude, and residual fuel up to C100+. C100+ data can be obtained using GC based techniques, such as comprehensive 2D GCxGC, and can also be related to the boiling point of the components using established compound group specific correlations. This has the advantage of availing detailed speciation of middle distillates and even light vacuum gas oil (VGO) samples in addition to the boiling curve, enabling the creation of compound family-specific boiling curves. The use of sulfur and nitrogen selective detectors, such as sulfur chemiluminescence (SCD) and nitrogen chemiluminescence detection (NCD), avails the boiling distributions of heteroatom components in petroleum crude oils and fractions up to VGO cuts.

Heavy petroleum fractions, such as VGO and VR samples, and heavy crude oils, can be speciated using high-resolution mass spectrometry, commonly through qualitative analysis. Typical means of petroleum component ionization include electrospray (ESI) and atmospheric pressure photoionization (APPI), and less frequently chemical derivation, or the addition of dopants for selective analysis. Some studies have also explored direct quantitative applications.

Saturated compounds are especially challenging to ionize as they undergo easy fragmentation in most common techniques. Various approaches have been reported for the detailed characterization of heavy petroleum saturates compounds: mass spectrometry with direct ionization or after derivation, high temperature gas chromatography, and molecular modeling. Field desorption (FD) was introduced as a soft ionization technique for thermally unstable substances in mass spectrometry. In recent years, chromatographic separation has enabled the detection of normal and isoparaffins, and some naphthenic compounds in crude oils. Applications of FD-MS using a commercial high-resolution time-of-flight mass analyzer can be used to characterize hydrocarbon species in separated saturates fractions. Techniques can use probability density functions to model the distribution of naphthenic rings, which allows to deconvolute and exclude potentially entrained aromatic components.

The analytical methods typically produce a description of the sample composition that encompasses the following attributes for each sample component: the number and type of heteroatoms, such as the number of sulfur, nitrogen, and oxygen atoms, the number of carbon atoms, and the number of hydrogen atoms relative to the carbon and hetero atoms. Numbers of atoms, for example, can be expressed as a double bond equivalent (DBE) value following Equation (1), with carbon, hydrogen and nitrogen referring to the number of the respective atoms in each molecular component:

$$DBE = Carbon - Hydrogen/2 + Nitrogen/2 + 1 \quad (1)$$

Boiling Point Model

The AEBP of individual molecular parameters of a petroleum composition has been previously described. Briefly, the AEBP of each individual component can be calculated using an empirical model combining three components; a carbon number dependent part combined with a sulfur atom and DBE co-dependent part (A), and a DBE dependent term (B), Equation (2):

$$AEBP = 236.45 \times \ln(C\# + A_{(S\#,DBE)}) - 360.31 + B_{(DBE)} \quad (2)$$

In Equation (2), A, and B may depend on the number of sulfur atoms (S #) and DBE value in the component under analysis, as defined in Equations (3), (4), and (4a), below:

$$A = (-0.1447 \times DBE + 3.7578) \times S\# \quad (3)$$

If DBE is less than 10, then:

$$B_{(DBE \leq 10)} = -0.751 \times DBE + 8.270 \quad (4)$$

Otherwise, if DBE greater than, or equal to, 10, then:

$$B_{(DBE \geq 10)} = -0.00565 \times DBE^2 + 0.583 \times DBE - 2.720 \quad (4a)$$

The boiling curve of a speciation data set can be obtained by calculating the AEBP for each identified component, sorting the components by their AEBP, and calculating the summed abundance with increasing AEBP Analytical Characterization to Obtain Composition Information Composition information can be obtained from a separation tools capable of speciating petroleum samples, for instance gas chromatography, two dimensional gas chromatography, or high-resolution mass spectrometry, or ultra-high-resolution mass spectrometry. Specific experimental conditions related to examples of the present disclosure are described in the following sections.

Comprehensive Two-Dimensional Gas Chromatography

The determination of hydrocarbon group types (by aromatic ring families) and sulfur speciation in heavy distillate cuts using GCxGC are previously described. In experiments, two-dimensional gas chromatography was performed using 7890 Agilent GCs (Agilent Technologies, Santa Clara, California, USA) with a single loop modulation systems from Zoex (ZX1 model, Zoex Corporation, Houston, Texas, USA).

One GC was equipped with an FID from Agilent (Santa Clara, California, USA), operated with the following parameters as described elsewhere. A sample was injected under typical separation conditions onto a non-polar/polar column configuration with helium as the carrier gas. The separation was modulated with a single loop and detection of components achieved with an FID operated with typical parameters.

Another GC was operated with a SCD model 355 under typical conditions described in the literature. A sample was injected under typical separation conditions onto a non-polar/polar column configuration with helium as the carrier gas. The separation was modulated with a single loop and sulfur selective detection of components achieved with an SCD operated with typical parameters.

Data processing was achieved using Chemstation software version B.1.04 (Agilent Technologies, Santa Clara, California, USA) and GC image software v2.1software (Zoex Corporation, Houston, Texas). The identification of compounds was based on standard compound and literature reported retention times. Quantification was achieved by normalization of the chromatogram to the total chromatogram area.

Photoionization High-resolution Mass Spectrometry

Atmospheric pressure photoionization (APPI) FT-ICR MS was conducted as previously described. Briefly, a 9.4 T Apex Qe Fourier transform ion cyclotron resonance mass spectrometer was used with an APPI source, operated in the positive polarity mode with parameters described elsewhere. Samples were dissolved in toluene (Honeywell, Chromasolv grade for HPLC≥99.9%) and diluted to a final concentration of 10 µg/mL for the FT-ICR MS measurements. Ion transfer parameters were tuned based on prior analysis of the sample using a time-of-flight mass spectrometer (Agilent Technology G6230B TOF-MS with APPI source) by visually matching the mass signal distributions as described before. Key parameters for this work were ion accumulated in the collision cell for 0.1 s before transfer to the ICR cell for high-resolution mass measurement, with funnel RF voltage tuned between 80 V and 190 V, typically 110 V, and ion transfer time between 0.8 milliseconds (ms) and 1.6 ms for each experiment, typically 1.1 ms for lighter cuts and up to 1.4 ms for the heavy samples. 128 scans with 4M data points were recorded and processed as described before. Only radical cations [M•+] as the most representative ion species, and their 13C and 34S isotope signals were considered.

Field Desorption Mass Spectrometry

The saturated compounds in selected samples were separated on alumina by elution with pentane, as described elsewhere, and then characterized with field desorption (FD) mass spectrometry using an AccuTOF GCx-plus time-of-flight mass spectrometer (JEOL, Japan) with FD ion source as previously reported. The emitter was kept at 10 kV and extraction electrodes at 2.4 kV. The ion extraction was tuned using acetone as reference before the measurement, and the instrument calibrated and performance checked using PEG1000 solution in toluene. Standard and samples were diluted to 1 mg/mL in toluene and carefully adsorbed onto a JEOL FD/FI emitter which was mounted on the FD probe. The loaded probe was transferred swiftly into the ion source, and the analysis started by ramping the emitter current from 0 mA to 40 mA at a rate of 12.8 mA/min. Ions were recorded from 35 m/z (where m/z represents mass divided by charge number) to 1,600 m/z for 3.2 minutes (200 s). Mass spectra were obtained in msAxel software (version 2.1, JEOL, Japan) by averaging spectra over the time interval during which ions were generated. After mass recalibration, the centroid mass list was exported for peak identification in MS Excel. For each mass signal, the Kendrick mass defect (KMD) and modulo 14 was calculated, and the signals assigned against tabulated values for HC class DBE series. The 13C isotope signals [M+1] matched the theoretical abundance and were added to each compound's abundance.

EXAMPLES

Example 1

In a first example, a liquid petroleum cracking product with components boiling from 200° C. to 700° C. was speciated using GCxGC with flame ionization detector (FID) and GCxGC sulfur chemiluminescence detector (SCD) and by atmospheric pressure photo ionization Fourier-transform ion cyclotron resonance mass spectrometry (APPI FT-ICR MS). The isolated fraction of saturated compounds, obtained by microscale liquid chromatographic separation, was speciated by field desorption time-of-flight mass spectrometry (FD TOF MS). A 2-dimensional gas chromatogram with main aromatic compound families identified by their carbon number is described with reference to FIGS. 4A-4B. From the chromatogram, an inadequate resolution of the heavy compounds is apparent, as unresolved blobs above and right of the tetra-aromatic compounds. Missing these high-boiling components is expected and will be addressed through the use of mass spectrometry.

Figure 4A:
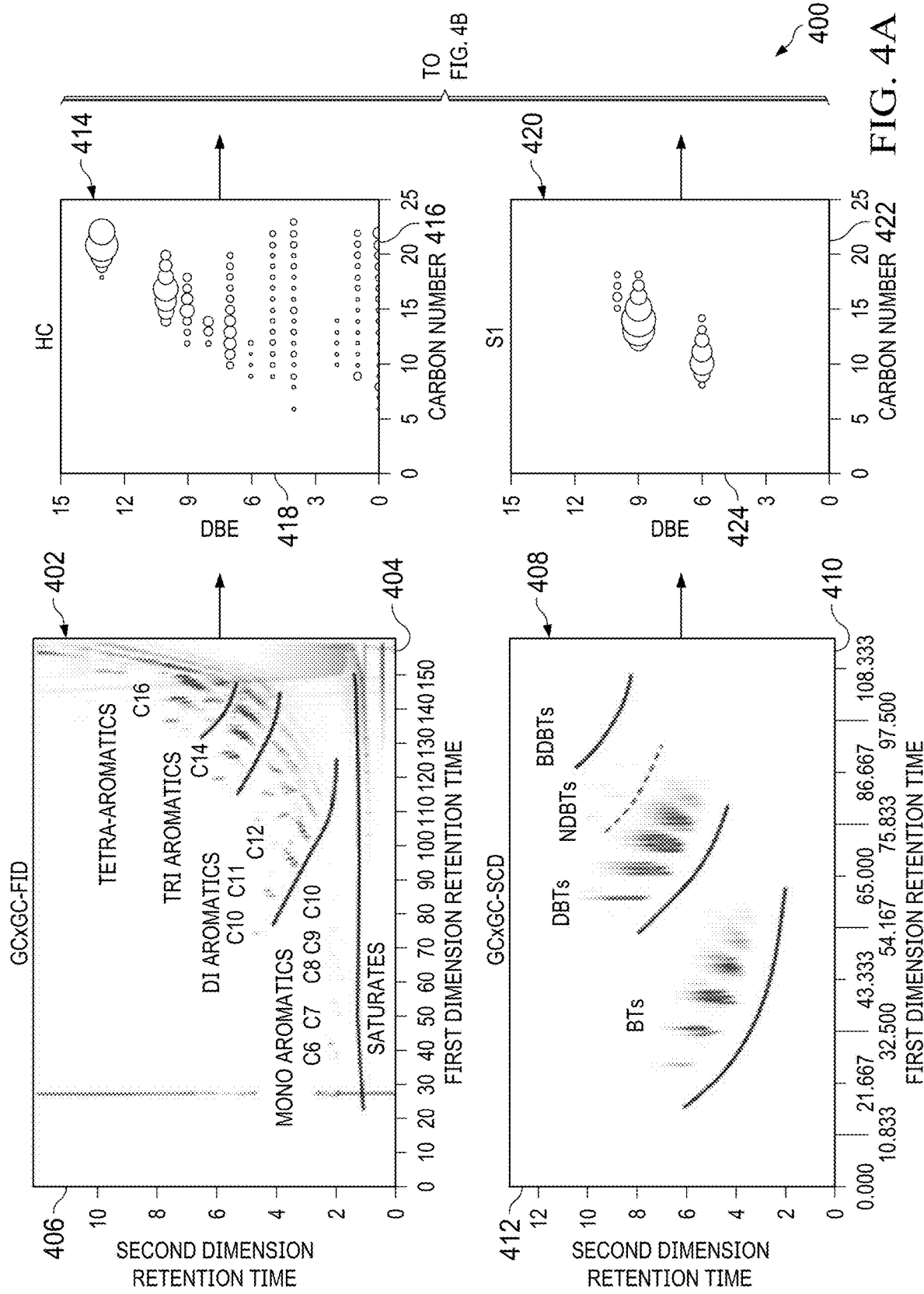
FIGS. 4A-4B are diagrams collectively showing an example of a workflow for determining the coverage of a two-dimensional (2D) gas chromatography (GCxGC) flame ionization detector (FID) and sulfur chemiluminescence detector (SCD) data set for a wide-boiling range sample, according to some implementations of the present disclosure.
Figure 4B:
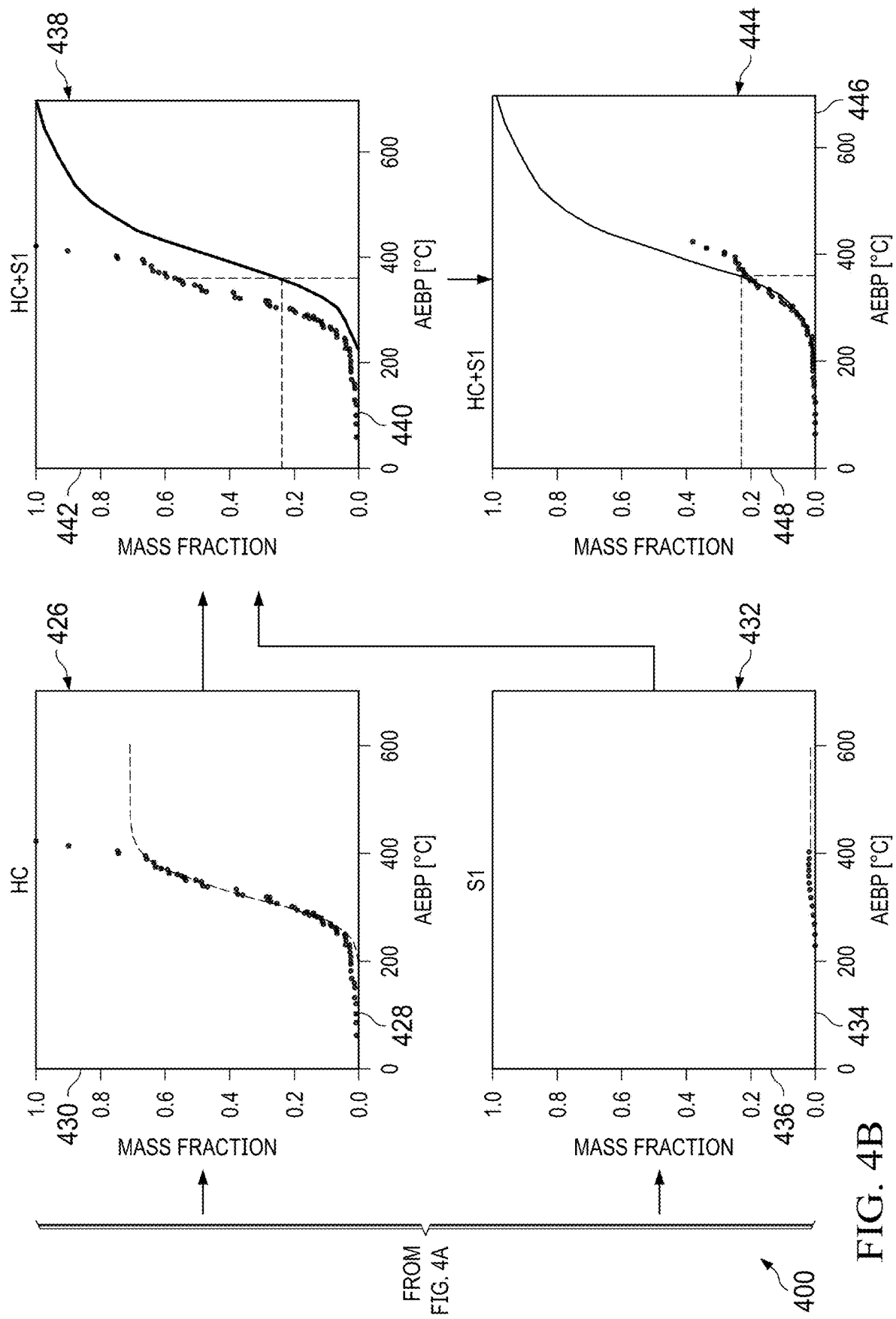

FIGS. 4A-4B are diagrams collectively showing an example of a workflow 400 for determining the coverage of a GCxGC-FID data set for a wide-boiling range sample, according to some implementations of the present disclosure. FIG. 4A includes a graph 402 of a 2D chromatogram showing hydrocarbon compounds obtained using GCxGC-FID. The graph 402 is plotted relative to $1^{st}$ dimension reference time 404 and a $2^{nd}$ dimension retention time 406. FIG. 4A also includes a graph 408 of a 2D chromatogram showing sulfur ($S_1$) species obtained using GCxGC-SCD. The graph 408 is plotted relative to $1^{st}$ dimension reference time 410 and a $2^{nd}$ dimension retention time 412. FIG. 4A also includes a plot 414 identifying carbon number and double bond equivalent (DBE) lumps of hydrocarbon. The plot 414 is plotted relative to carbon number 416 and DBE 418. FIG. 4A also includes a plot 420 identifying carbon number and double bond equivalent (DBE) lumps of sulfur components. The plot 420 is plotted relative to carbon number 422 and DBE 424.

FIG. 4B includes a graph 426 showing an example of a hydrocarbon compounds boiling curve associated with FIGS. 4A and 4C. The graph 426 is plotted relative to AEBP 428 and mass fraction 430. FIG. 4B also includes a graph 432 showing an example of a sulfur species boiling curve associated with FIGS. 4A and 4B. The graph 432 is plotted relative to AEBP 434 and mass fraction 436.

FIG. 4B also includes is a graph 438 showing an example of a curve combining a hydrocarbon compounds boiling curve of graph 426 and the sulfur species boiling curve of graph 432 using the GCxGC accessible components. It is important to note that the boiling curves represent the underlying composition in its entirety, including breakdown by carbon number, DBE and heteroatom class. The graph 438 is plotted relative to AEBP 440 and mass fraction 442.

FIG. 4B also includes a graph 444 showing an example of normalized hydrocarbon and sulfur components summed by AEBP (dots) and compared to SIMDIS curve (line). For example, the curves in graph 444 match AEBP and SIMDIS curves up to AEBP=360° C., representing 22.5% of the sample. The graph 444 is plotted relative to AEBP 446 and mass fraction 448. The following FIGS. 5 to 7 show some graphs in FIGS. 4A and 4B in larger scale.

Figure 5:
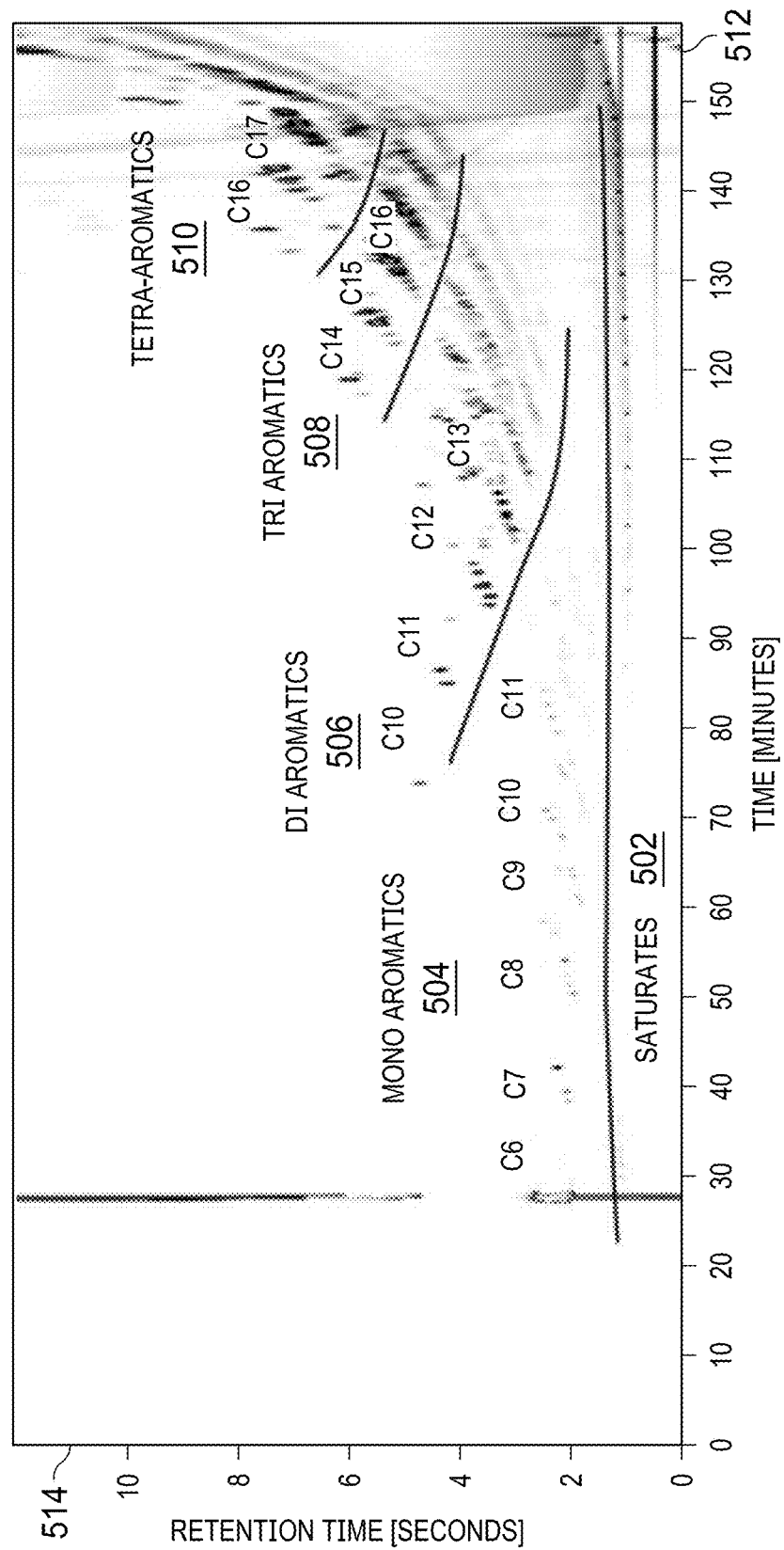
FIG. 5 is a graph showing an example of a two-dimensional gas chromatogram with compound families, according to some implementations of the present disclosure.

FIG. 5 is a graph 500 showing an example of a 2D gas chromatogram with compound families, according to some implementations of the present disclosure. Some carbon number groups are identified and indicated, including saturates 502, mono aromatics 504, di aromatics 506, tri aromatics 508, and tetra-aromatics 510. The carbon groups are plotted relative to a time 512 (e.g., in minutes) and retention time 514 (e.g., in seconds).

Figure 6:
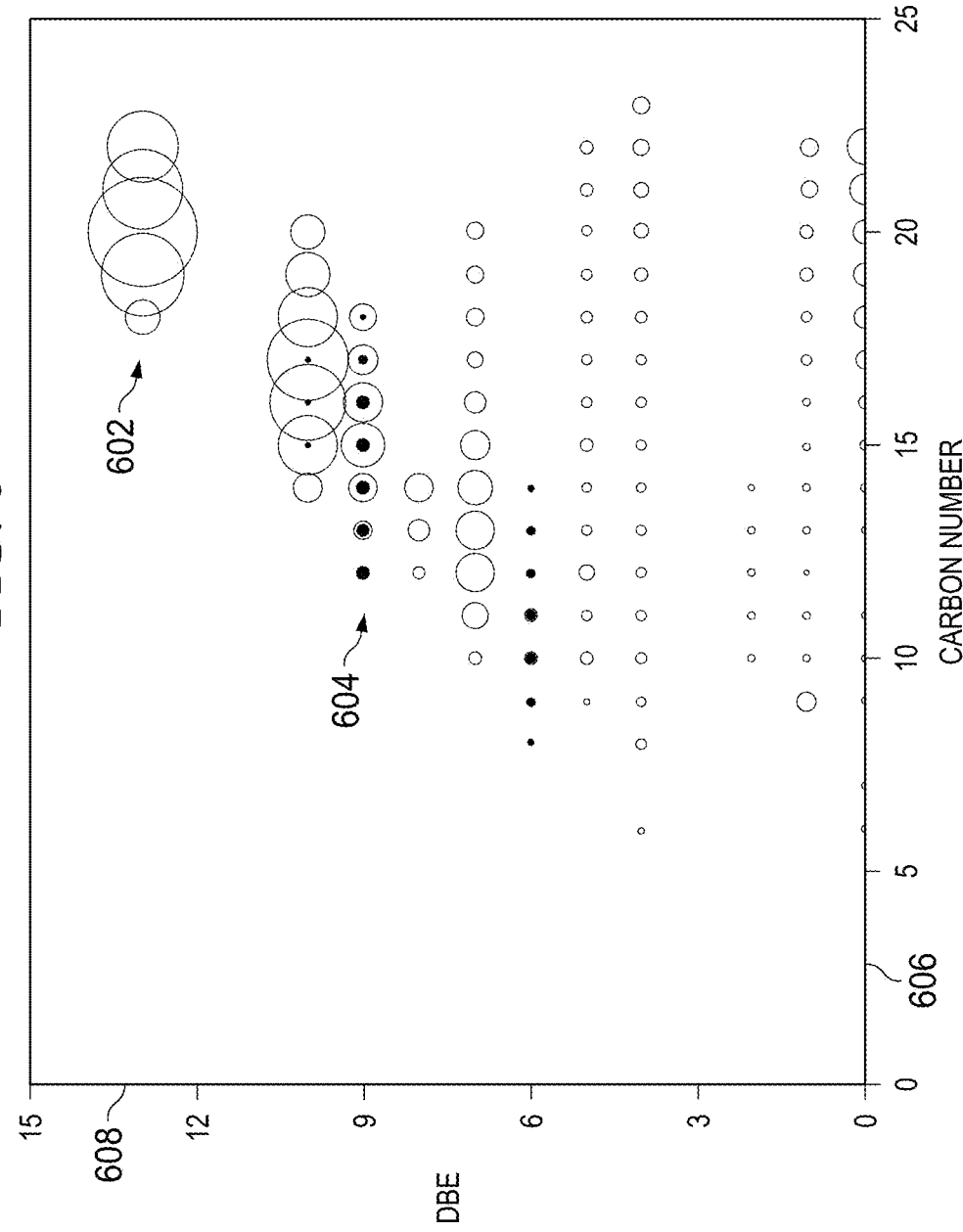
FIG. 6 is a graph showing an example of a representation of a composition model obtained using GCxGC, according to some implementations of the present disclosure.

FIG. 6 is a graph 600 showing an example of a representation of a composition model obtained using GCxGC, according to some implementations of the present disclosure. Each dot in the graph 600 represents a compound family 602 with the same number of aromatic and naphthenic rings, and with the same number of carbon atoms. Sulfur compounds 604 are also included, indicated by solid circles inside the dots representing carbon. The area of the dots represents the summed signal intensity per component. The circles and dots are plotted relative to carbon number 606 and DBE 608.

FIG. 6 is an example of a composition model obtained of the 2D gas chromatographic characterization, according to some implementations of the present disclosure.

The composition model was used to calculate the boiling distribution as a collection of individual boiling points of the modeled components. The boiling curves of pure hydrocarbon and sulfur compounds are shown in FIG. 7. The measured SIMDIS curve is included for comparison in the plot. Due to the presence of many high boiling components that elude speciation by GCxGC, the modeled curves are shifted to the left compared to the SIMDIS curve.

FIG. 7 is a graph 700 showing an example of AEBP curves calculated based on the GCxGC based composition model, according to some implementations of the present disclosure. Note that the GCxGC derived boiling curves for HC 702 and S$_1$ 704 together are normalized to 1. SIMDIS curve 706 of the entire sample is shown for comparison. The sample was analyzed using mass spectrometry to speciate the high- and non-boiling components.

Figure 8A:
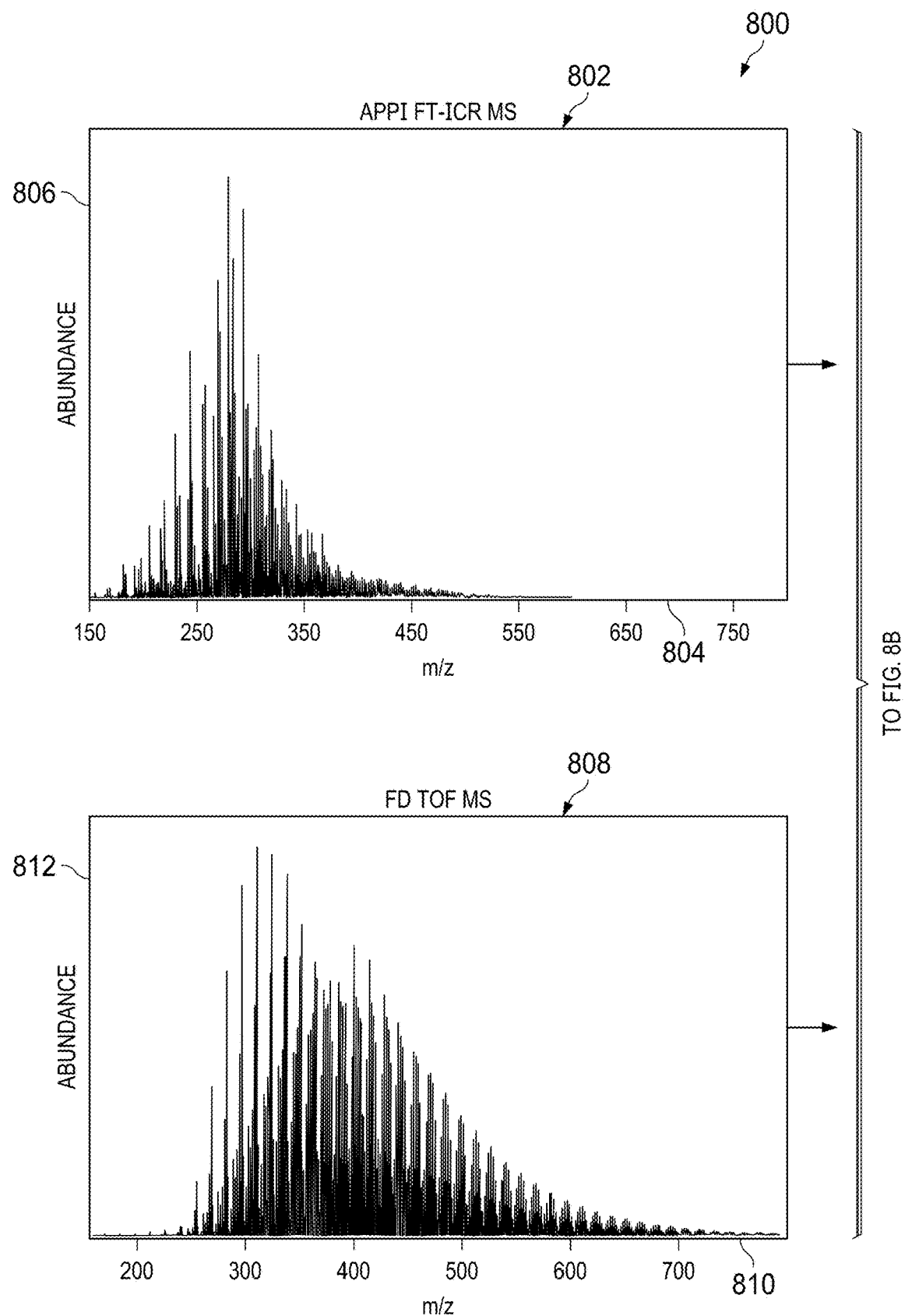
FIGS. 8A-8C are diagrams collectively showing an overview of a workflow of mass spectrometry data processing steps, according to some implementations of the present disclosure.
Figure 8B:
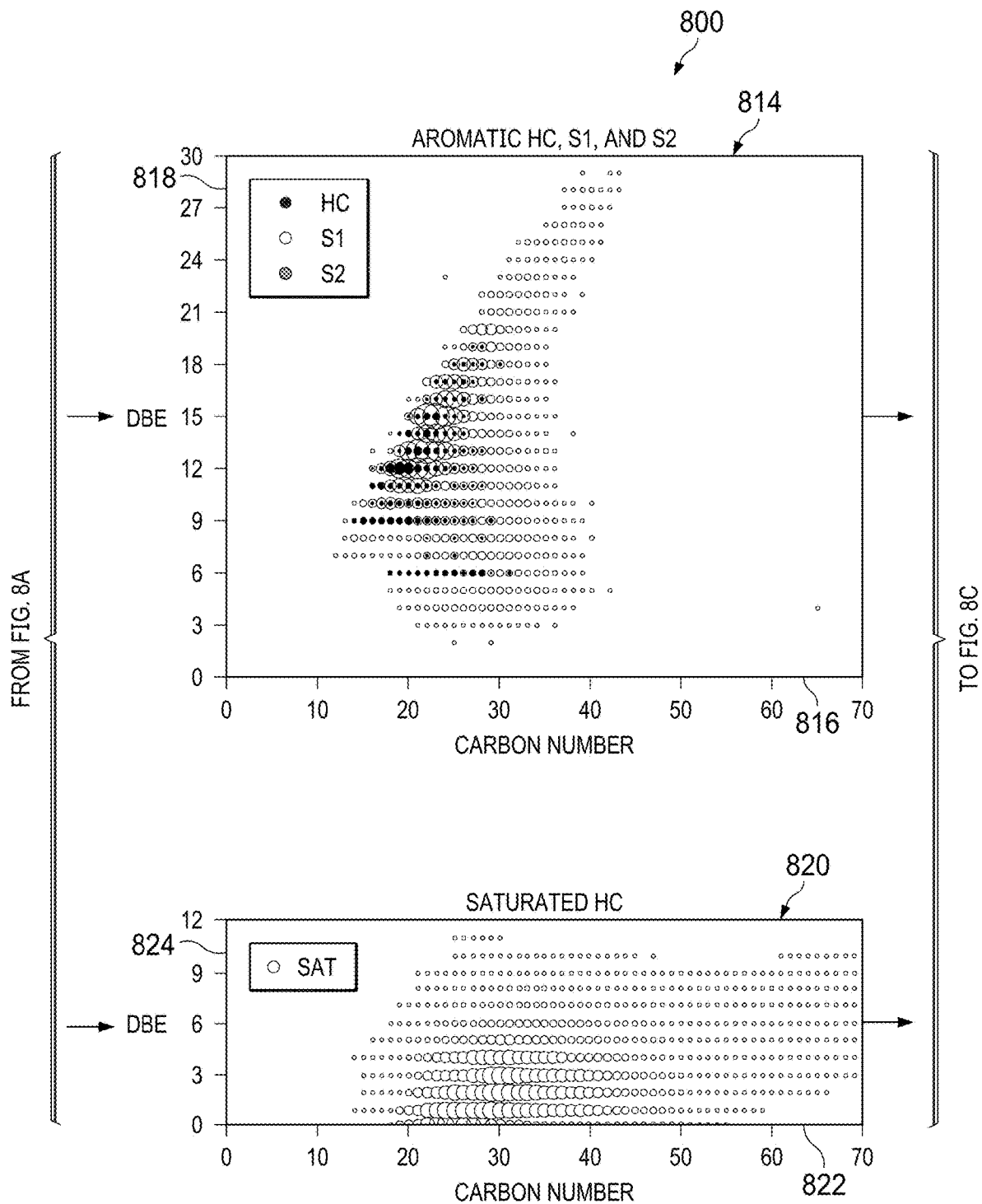
Figure 8C:
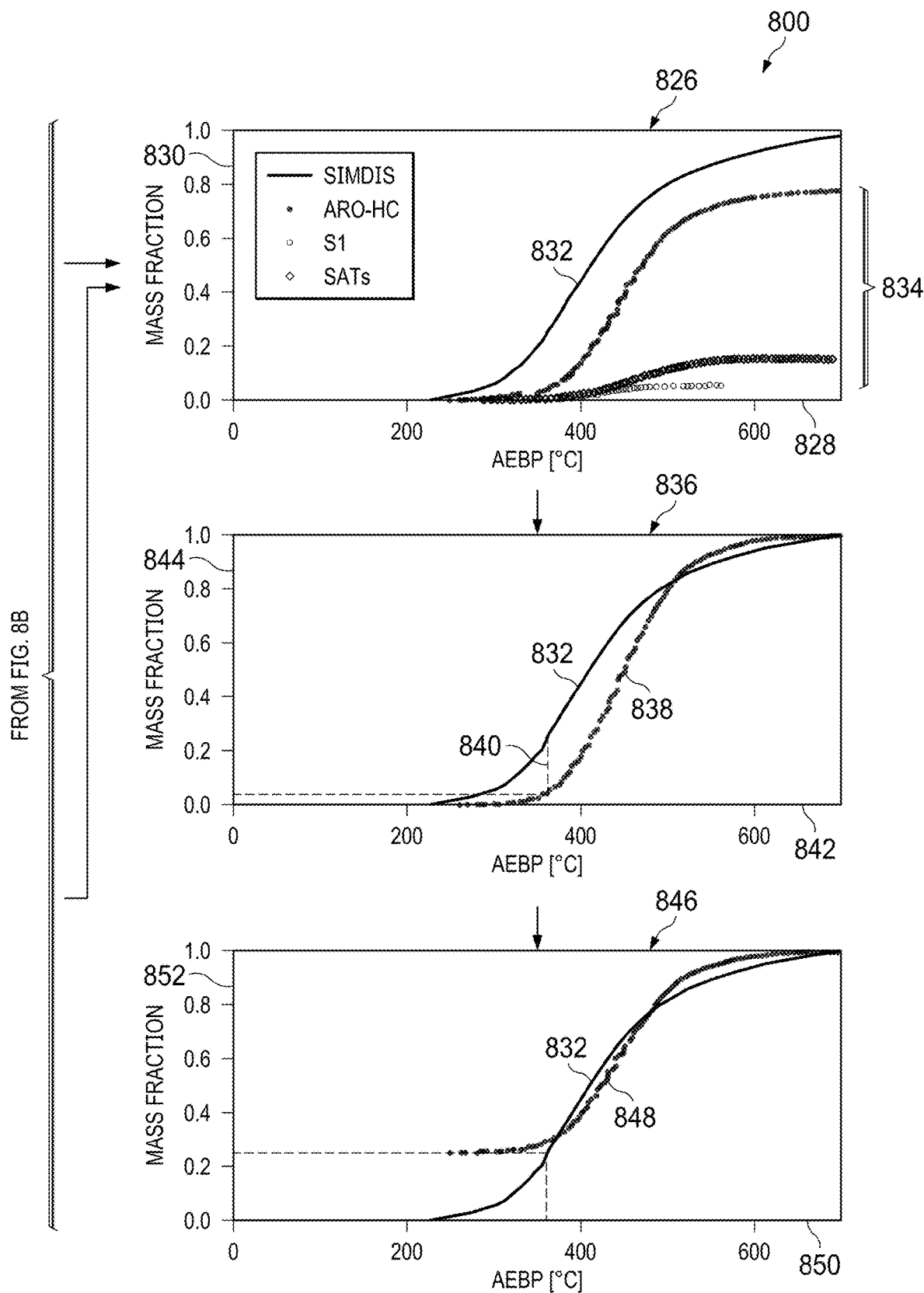

FIGS. 8A-8C are diagrams collectively showing an overview of a workflow 800 of mass spectrometry data processing steps, according to some implementations of the present disclosure. Referring to FIG. 8A, graph 802 shows APPI FT-ICR MS mass spectrum of the aromatic hydrocarbon and sulfur compounds. The graph 802 is plotted relative to m/z 804 and abundance 806.

Graph 808 shows FD TOF MS mass spectrum of the saturated compounds separated by liquid chromatography. The graph 808 is plotted relative to m/z 810 and abundance 812.

Referring to FIG. 8B, graph 814, based on graph 802, shows the identified carbon number 816 and DBE 818 lumps of aromatic hydrocarbon and sulfur components. Graph 820, based on graph 808, shows an identified carbon number 822 and DBE 824 lumps of saturated hydrocarbons.

Referring to FIG. 8C, graph 826, based on graphs 814 and 820, shows respective boiling curves relative to AEBP 828 and mass fraction 830. Graph 826 and curves 834 are plotted relative to SIMDIS curve (line) 832, and share identical x-axes (AEBP 828) and mass fraction 830. The AEBP curves are for separate classes, normalized to their relative abundance.

Graph 836 shows a combined AEBP curve 838. An intersection line 840 indicated with a vertical dotted line at 360° C. represents the SIMDIS mass fraction covered by the data, relating to the highest boiling 77.5% of the sample. Curves in graph 836 are plotted relative to AEBP 842) and mass fraction 844.

Graph 846 shows a matched AEBP and SIMDIS curve 848, derived from graph 836. Curves in graph 846 are plotted relative to AEBP 850 and mass fraction 852.

Figure 9:
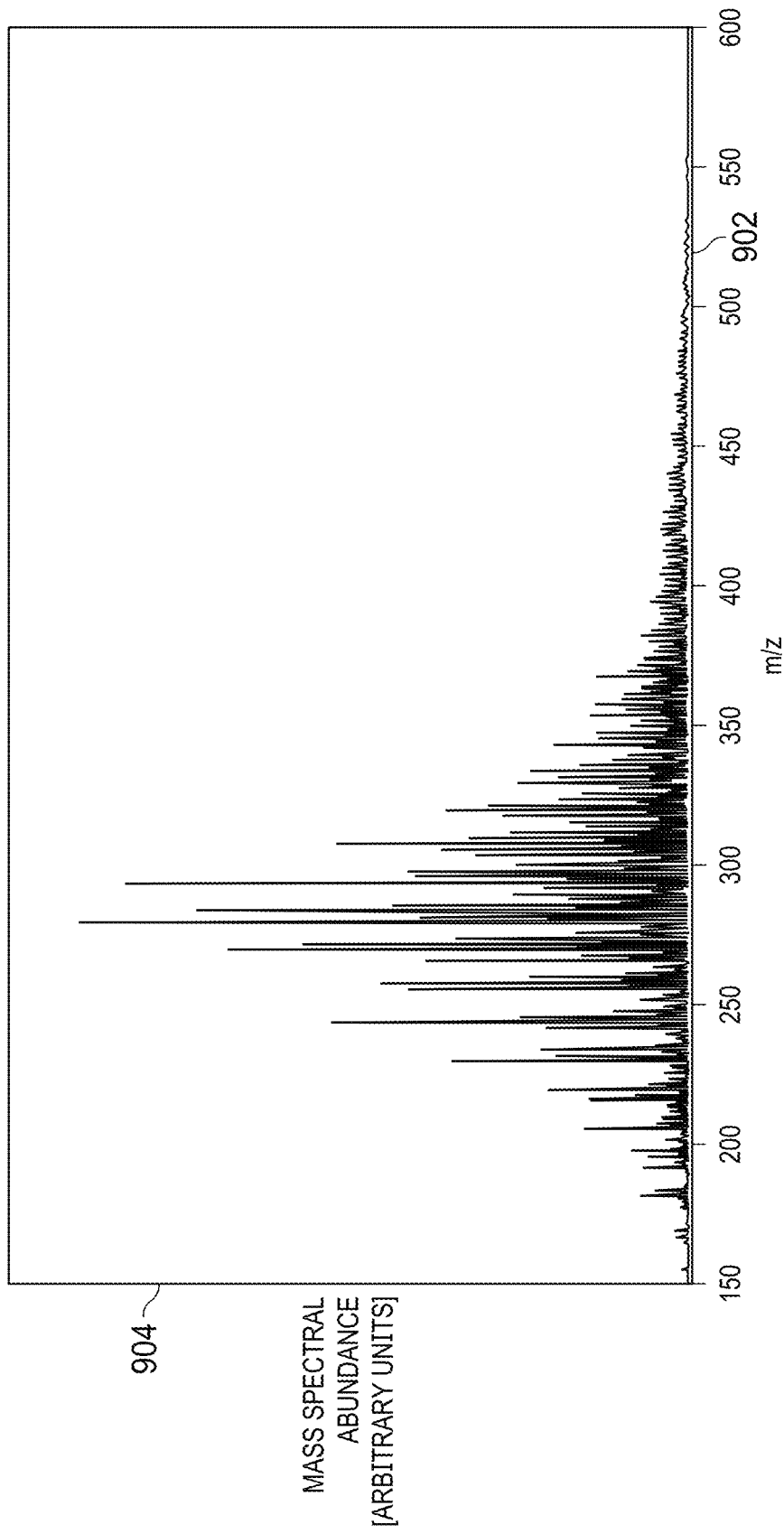
FIG. 9 is a graph showing an example of a high-resolution, atmospheric pressure photo ionization (APPI) mass spectrum, according to some implementations of the present disclosure.
Figure 10:
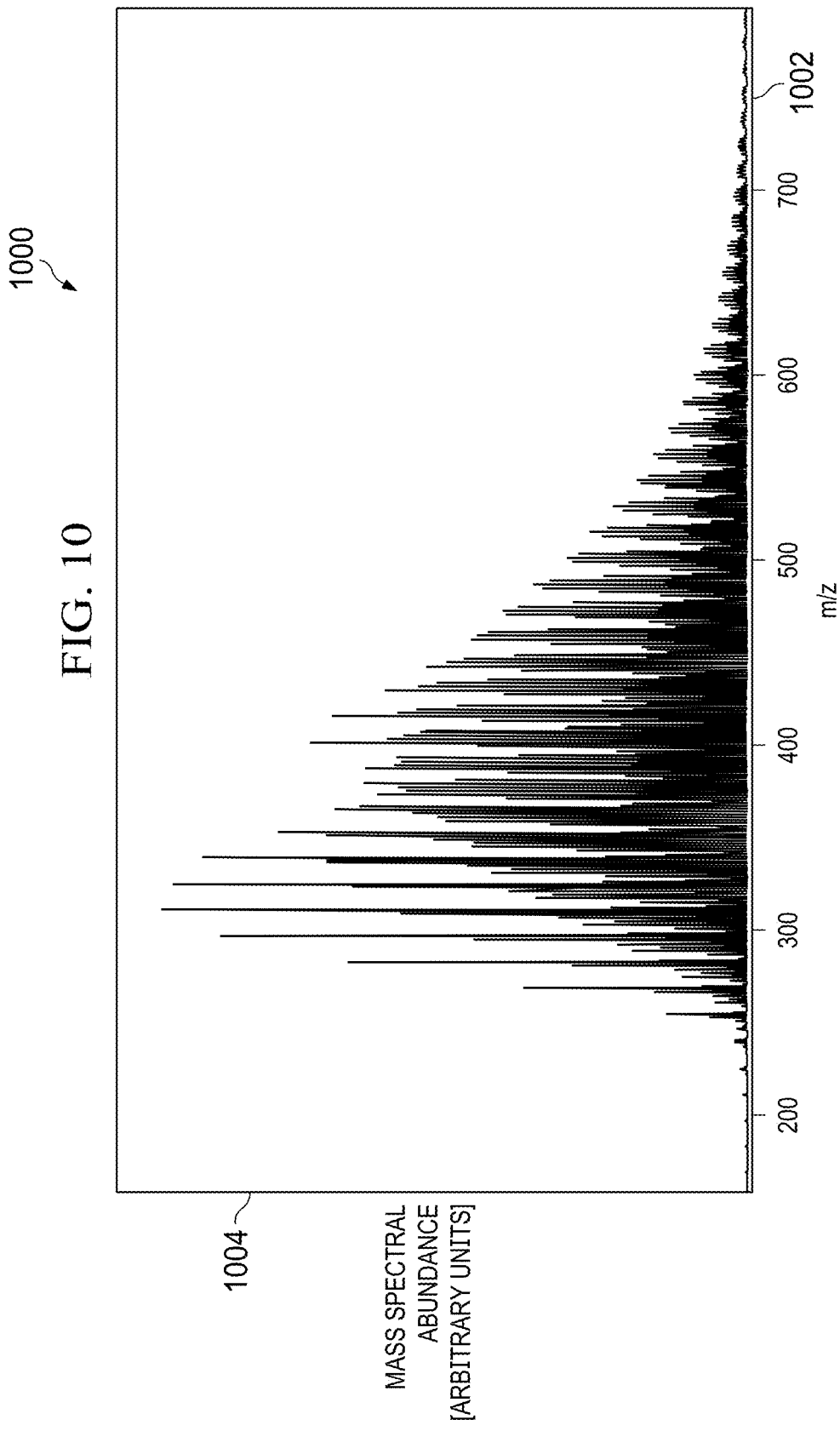
FIG. 10 is a graph showing an example of a field desorption time-of-flight mass spectrum of the saturated compound fraction, according to some implementations of the present disclosure.

FIG. 9 is a graph 900 showing an example of a high-resolution, APPI mass spectrum, according to some implementations of the present disclosure. The saturated compounds were isolated using micro scale liquid chromatography on solid phase extraction cartridge, weighed out for quantification, and then analyzed using FD TOF MS. The corresponding mass spectrum is shown in FIG. 10. The graph 900 is plotted relative to an m/z axis 902 and a mass spectral abundance 904, e.g., in arbitrary units.

Figure 11A:
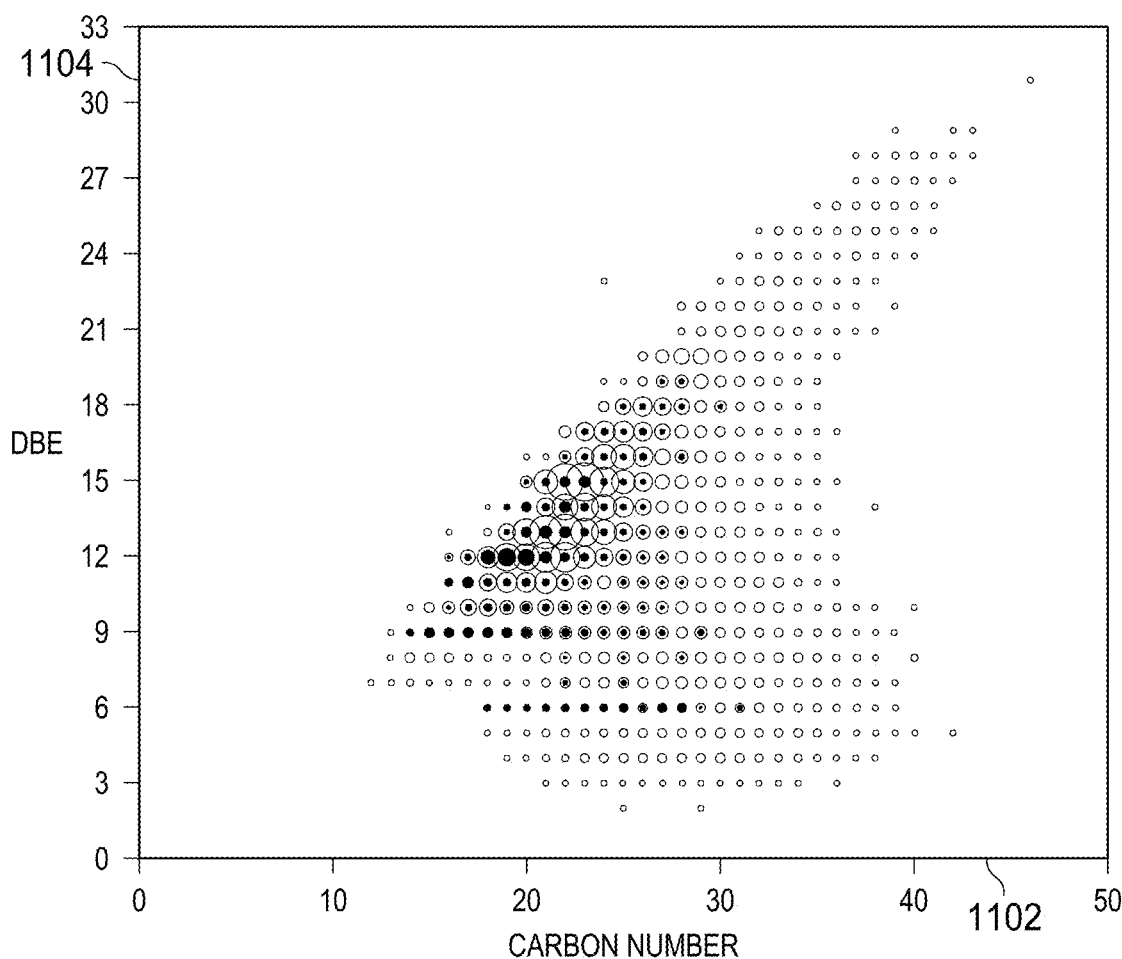
FIG. 11A is graph of an example of an APPI Fourier transform ion cyclotron resonance mass spectrometry (FT-ICR MS) derived composition model describing high boiling aromatic components, according to some implementations of the present disclosure.
Figure 11B:
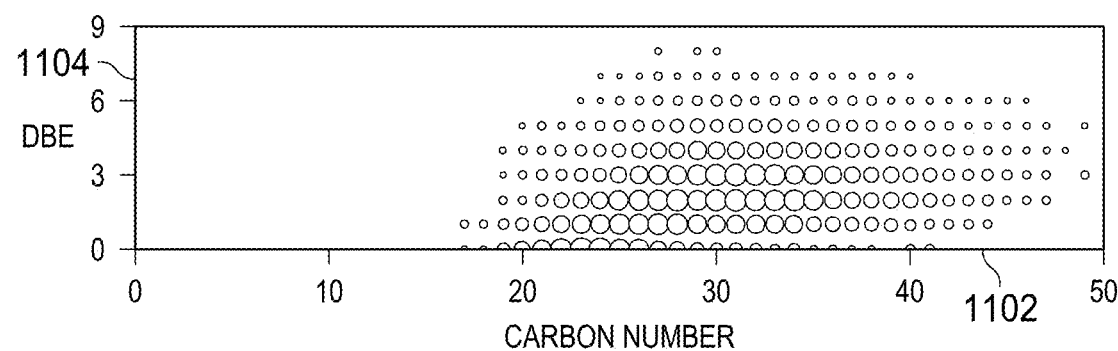
FIG. 11B is graph of an example of a Field desorption (FD) time-of-flight (TOF) MS derived composition model of the saturated components in the sample saturates fraction, according to some implementations of the present disclosure.
Figure 12:
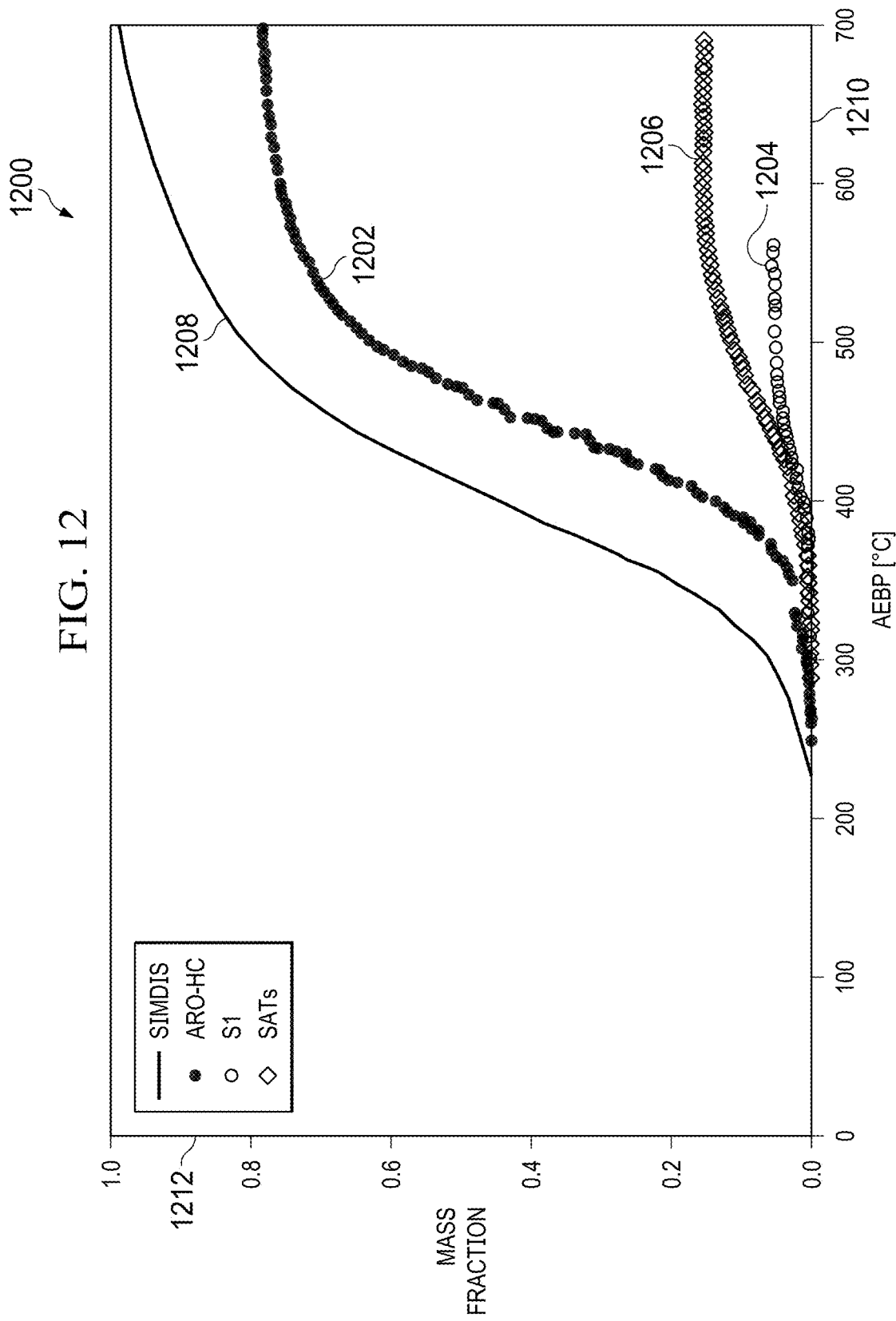
FIG. 12 is graph of an example of AEBP curves calculated based on the APPI FT-ICR MS and FD TOF MS composition models, according to some implementations of the present disclosure.

FIG. 10 is a graph 1000 showing an example of a field desorption time-of-flight mass spectrum of the saturated compound fraction, according to some implementations of the present disclosure. Both mass spectra were processed as described before to identify components by their number and type of heteroatoms, number of carbon atoms, and double bond equivalent (DBE). The resulting composition models are displayed in FIGS. 11A and 11B showing the aromatic hydrocarbon and sulfur compounds, and in FIG. 12 showing the saturated compounds. The graph 1000 is plotted relative to an m/z axis 1002 and a mass spectral abundance 1004, e.g., in arbitrary units.

FIG. 11A is graph 1100 of an example of an APPI FT ICR MS derived composition model describing high boiling aromatic components, according to some implementations of the present disclosure. The graph 1100 is plotted relative to a carbon number 1102 and a DBE 1104.

FIG. 11B is graph 1106 of an example of an FD TOF MS derived composition model of the saturated components in the sample saturates fraction, according to some implementations of the present disclosure. The graph 1106 is plotted relative to the carbon number 1102 and the DBE 1104.

The combined composition model (list of all identified components, including their carbon number, DBE value, and heteroatom content), was used to calculate the corresponding boiling distribution as a collection of individual boiling points of the modeled components. The boiling curves of pure hydrocarbon aromatic, saturated compounds, and sulfur compounds are shown in FIG. 12. The measured SIMDIS curve is included for comparison in the plot, due to the presence of many lower boiling components that elude detection by the mass spectrometric methods it is shifted to the left of the mass spectrometry-derived data.

FIG. 12 is graph 1200 of an example of AEBP curves 1202, 1204, and 1206 calculated based on the APPI FT-ICR MS and FD TOF MS composition models, according to some implementations of the present disclosure. For example, the graph 1200 is based on graphs 1100 and 1106. Note that the combined mass spectrometry derived boiling curves are normalized to 1. SIMDIS 1208 curve of the entire sample is shown for comparison. Curves in FIG. 12 are plotted relative to AEBP 1210 and mass fraction 1212.

Figure 13A:
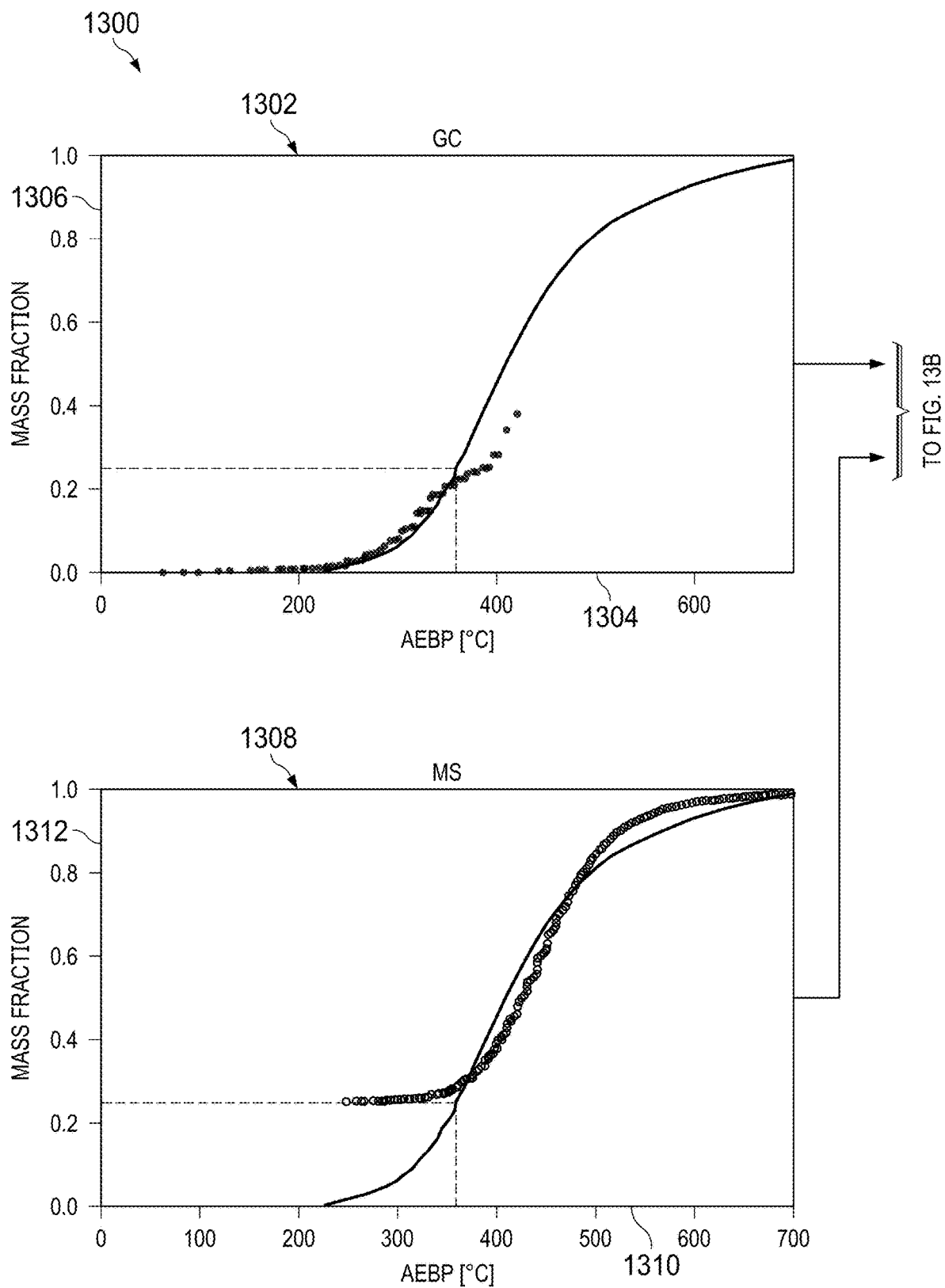
FIGS. 13A-13B are diagrams collectively showing an example of a workflow for combining boiling curves including underlying molecular speciation data sets, according to some implementations of the present disclosure.
Figure 13B:
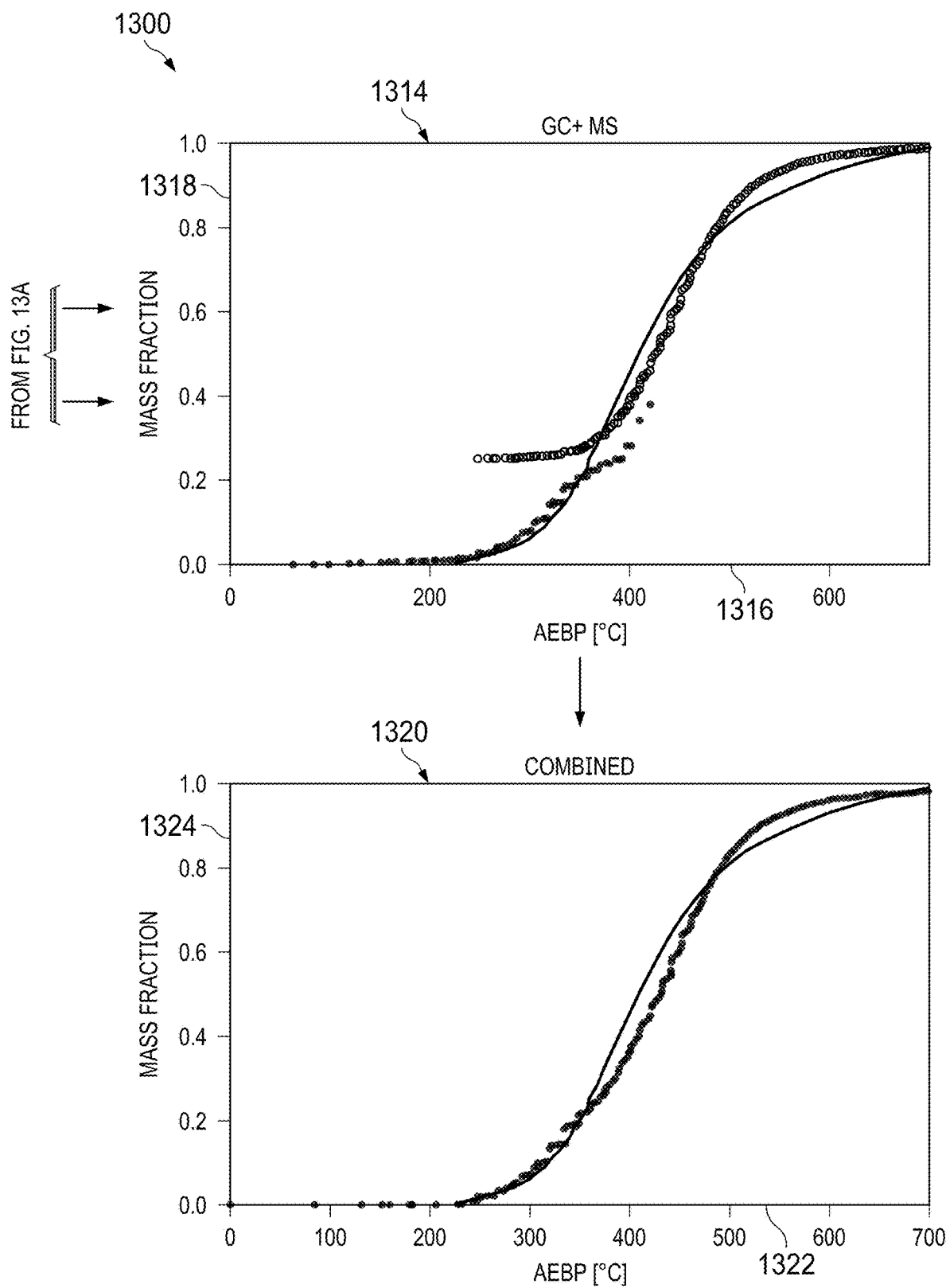

The combination of AEBP curves is shown in FIGS. 13A and 13B for a GC graph 1302 data sets (dots) and an MS graph 1308 data sets (dots), matching a GC+MS graph 1314 (the global SIMDIS curve of the sample) and a combined graph 1320 (combined data AEBP curve matches the SIMDIS curve). The underlying mass fractions have been scaled accordingly to give the quantitative component list of the sample.

FIGS. 13A-13B are diagrams collectively showing an example of a workflow 1300 for combining boiling curves including underlying molecular speciation data sets, according to some implementations of the present disclosure. Referring to FIG. 13A, the GC graph 1302 is plotted relative to AEBP 1304 and mass fraction 1306. The MS graph 1308 is plotted relative to AEBP 1310 and mass fraction 1312.

Referring to FIG. 13B, a GC+MS graph 1314, combining graphs 1302 and 1308, is plotted relative to AEBP 1316 and mass fraction 1318. The combined graph 1320, derived from graph 1314, is plotted relative to AEBP 1322 and mass fraction 1324.

Figure 14:
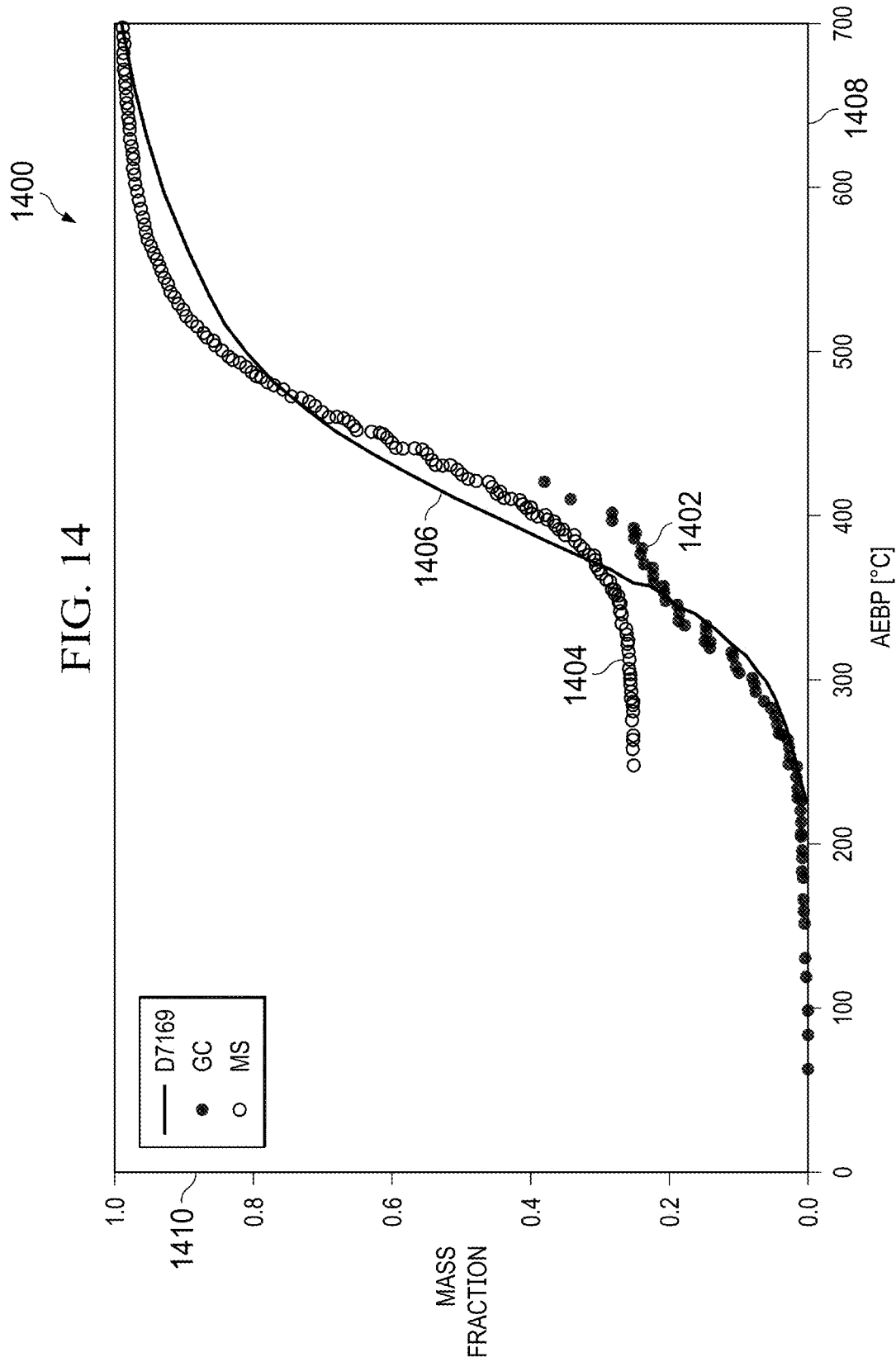
FIG. 14 is a graph showing an example of a combined GC+MS curve, according to some implementations of the present disclosure.
Figure 15:
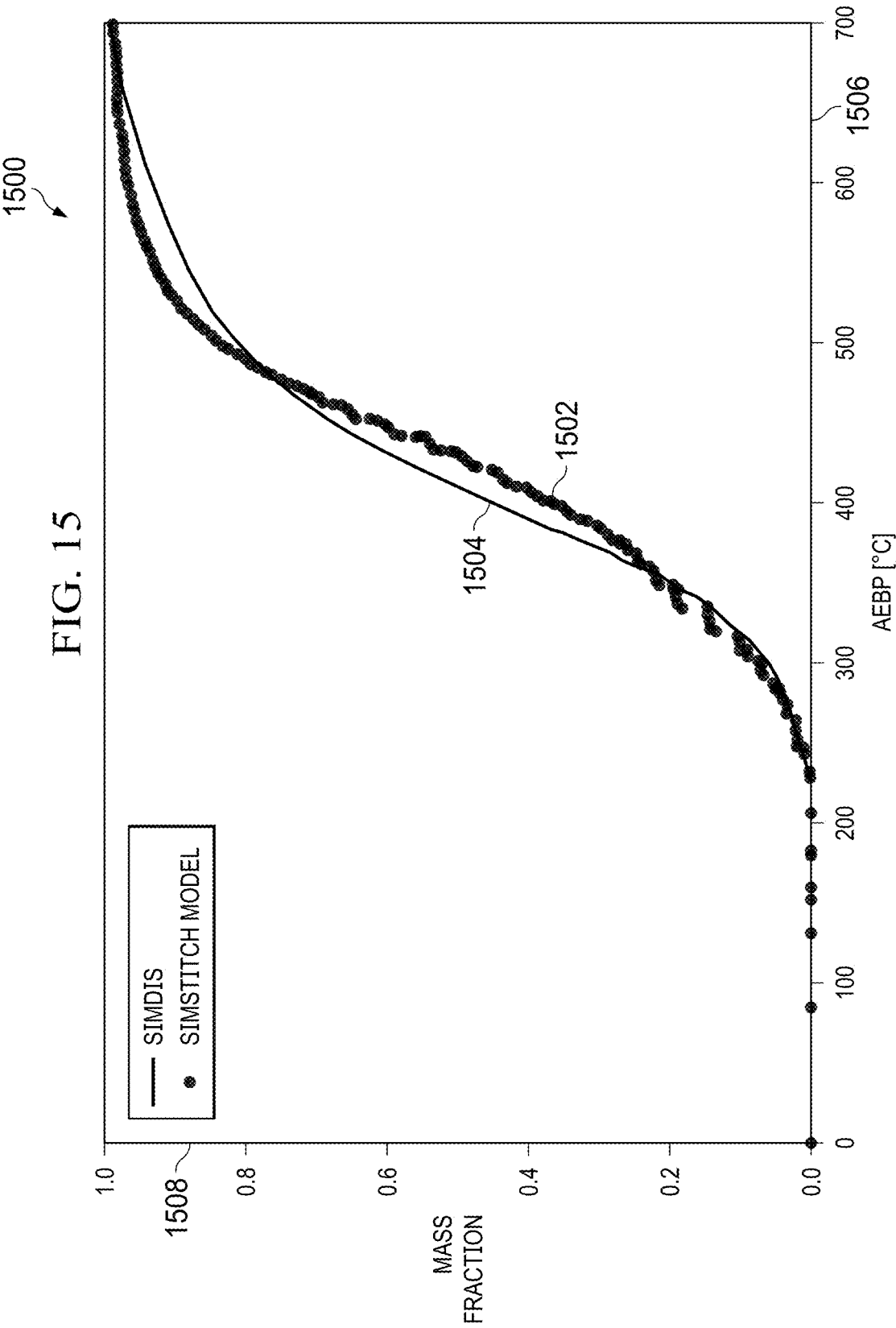
FIG. 15 is a graph showing an example of a unified SIMSTITCH AEBP curve vs SIMDIS measured curve, according to some implementations of the present disclosure.

Detailed views of graphs 1314 and 1320 are shown in FIGS. 14 and 15, respectively. The combined GCxGC data, matched against the SIMDIS boiling curve, indicates an accurate coverage up to 360° C. for this sample, FIG. 14. In the same plot, the mass spectrometry-derived boiling curve is also shown and covers components boiling above 360° C. The composition models can be combined. A stepwise blend of the compositions can be done, in this case it was done to achieve a smooth transition between 300° C. and 400° C. The result is shown in FIG. 15 where the unified composition boiling curve (dots) is compared to the SIMDIS curve (line).

FIG. 14 is a graph 1400 showing an example of a combined GC+MS curve, according to some implementations of the present disclosure. Graph 1400 includes stacked AEBP curves 1402 and 1404, obtained for 2D gas chromatography (GC) and APPI FT-ICR MS and FD TOF MS (MS) data sets, respectively. A SIMDIS curve 1406 of the entire sample is shown for comparison. Curves of graph 1400 are plotted relative to AEBP 1408 ad mass fraction 1410.

FIG. 15 is a graph 1500 showing an example of a unified SIMSTITCH AEBP curve 1502 vs SIMDIS measured curve 1504, according to some implementations of the present disclosure. Curves of graph 1500 are plotted relative to AEBP 1506 and mass fraction 1508.

Figure 16:
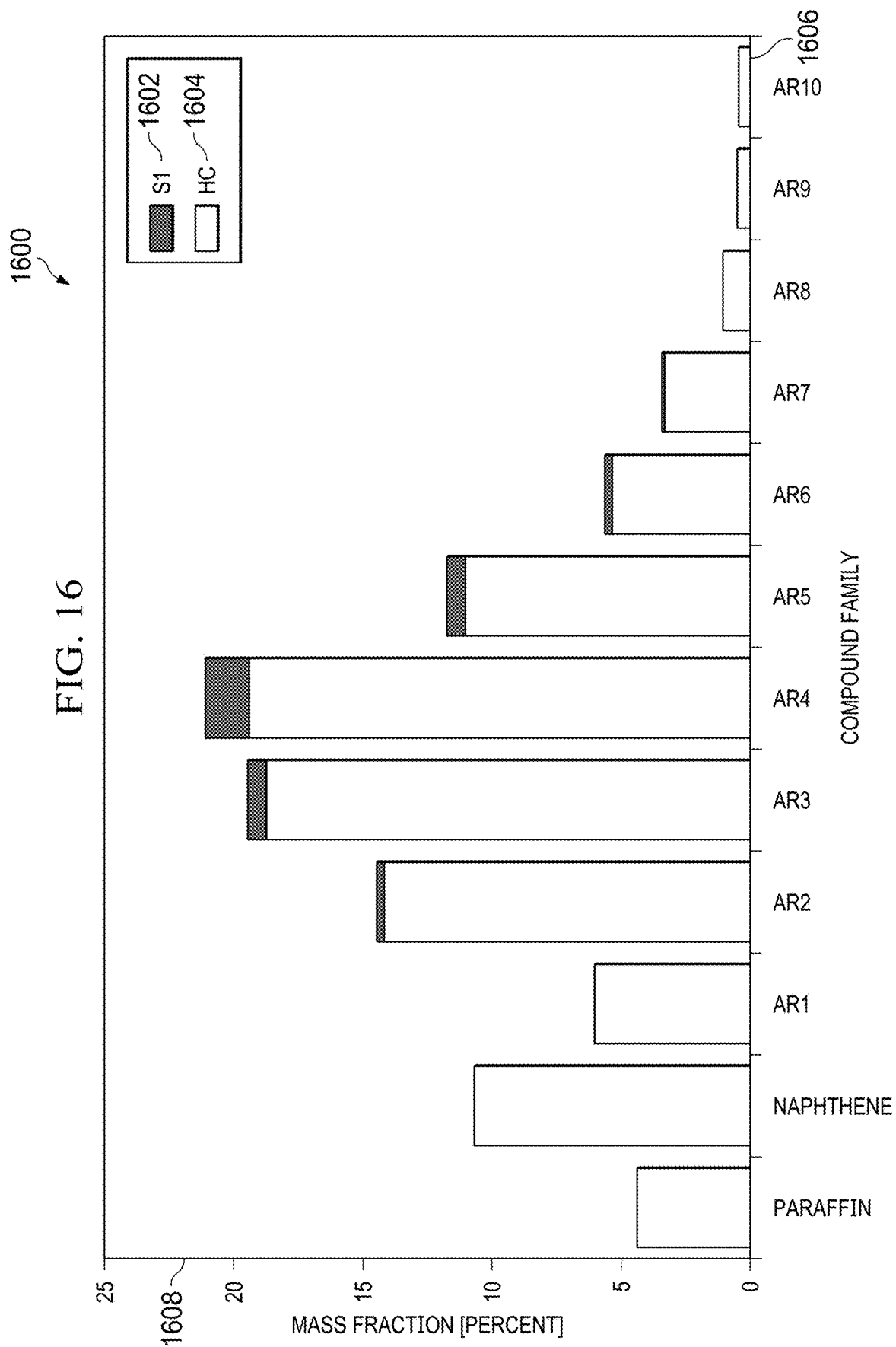
FIG. 16 is a bar graph showing example composition data by compound family, according to some implementations of the present disclosure.
Figure 17:
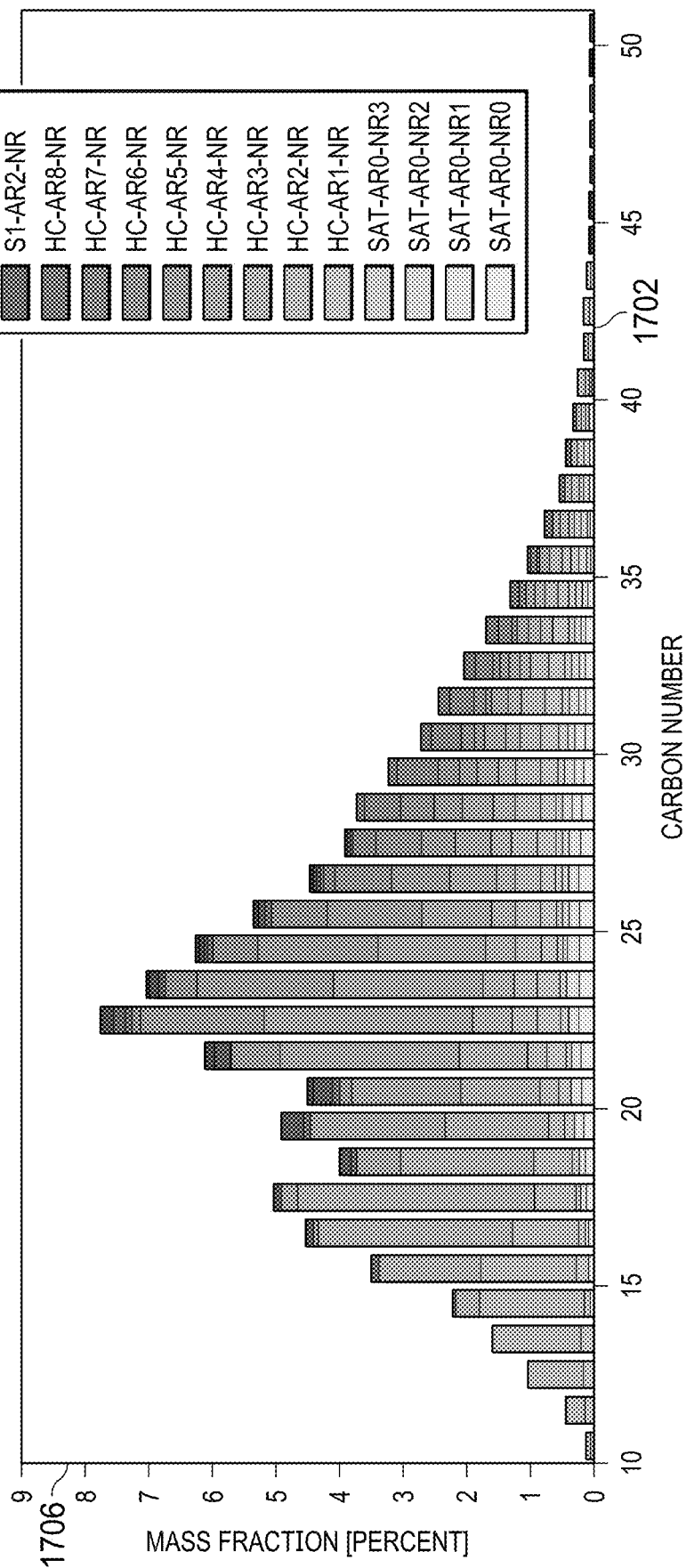
FIG. 17 is a bar graph showing an example alternative display of the same composition data as shown in FIG. 16, according to some implementations of the present disclosure.

Table 1 shows examples of molecular details captured in the model, with chemical and boiling information listed for each component and with the component family, number of aromatic rings (AR #), number of carbon atoms (C #), DBE value, mass fractions (MF) of the component, AEBP in ° C., and the cumulative mass fraction (cMF). The entire data set for this example includes 1,159 components, but is truncated for brevity. This composition can be compiled depending on the chemical information of interest. FIGS. 16 and 17 show the distribution by component family and number of aromatic rings, and the component family breakdown by carbon number, respectively.

TABLE 1

Chemical and Boiling Information, By Component

| Family | AR# | C# | DBE | MF | AEBP [° C.] | cMF |
|---|---|---|---|---|---|---|
| HC | 1 | 6 | 4 | 2.30E−05 | 84.4 | 2.30E−05 |
| SAT | 0 | 8 | 0 | 1.00E−06 | 131.4 | 2.40E−05 |
| HC | 1 | 8 | 4 | 2.58E−04 | 152.4 | 2.82E−04 |
| SAT | 0 | 9 | 0 | 7.00E−06 | 159.2 | 2.89E−04 |
| HC | 1 | 9 | 4 | 1.02E−03 | 180.3 | 1.31E−03 |
| HC | 1 | 9 | 5 | 8.12E−05 | 181.8 | 1.39E−03 |
| HC | 1 | 9 | 6 | 2.21E−05 | 181.8 | 1.41E−03 |
| SAT | 0 | 10 | 0 | 2.80E−05 | 184.1 | 1.44E−03 | continued for the entire composition (1159 total entries)

FIG. 16 is a bar graph 1600 showing example composition data by compound family, according to some implementations of the present disclosure. Hydrocarbon compounds 1602 are shown in white-fill, and sulfur containing compounds 1604 are shown in black fill. AR denotes the number of aromatic rings per molecule. Bars in the bar graph 1600 show different compound families 1606 and are graphed relative to mass fraction 1608.

FIG. 17 is a bar graph 1700 showing an example alternative display of the same composition data as shown in FIG. 16, according to some implementations of the present disclosure. In FIG. 17, the bar graph 1700 shows a carbon number 1702 breakdown for the individual compound families 1704, plotted relative to mass fraction 1706. A legend for the individual compound families 1704 indicates a three part compound identifier including: 1) a compound type, including: saturated (SAT) compounds, aromatic hydrocarbon (ARO) compounds, and sulfur containing compound ($S_1$); 2) a number of aromatic rings (AR #); and 3) a number of naphthenic rings (NR) for saturated compounds. For aromatic compounds, all potential naphthenic rings are summed.

Figure 18:
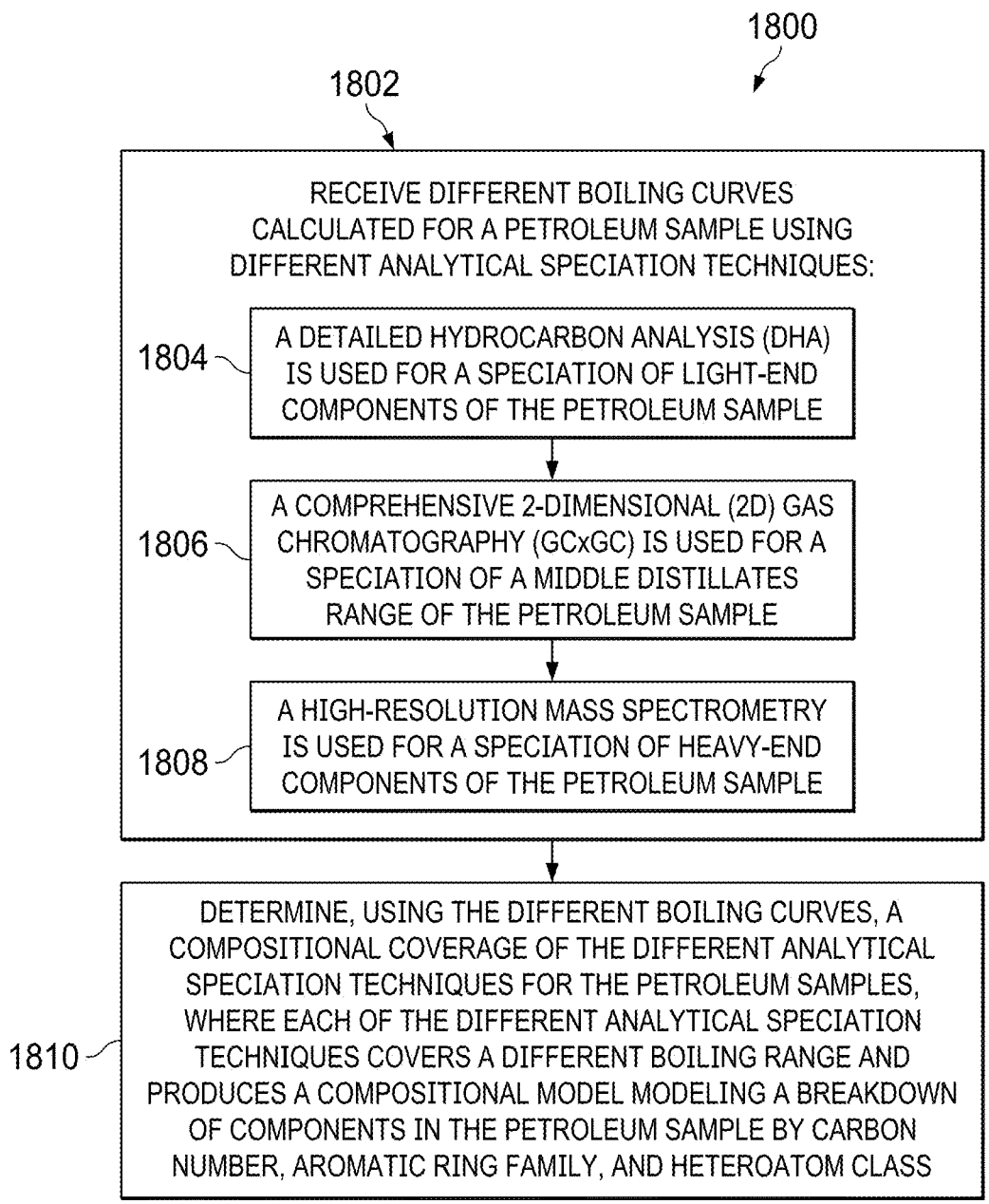
FIG. 18 is a flowchart of an example of a method for analyzing petroleum samples, according to some implementations of the present disclosure.

FIG. 18 is a flowchart of an example of a method 1800 for analyzing petroleum samples, according to some implementations of the present disclosure. For clarity of presentation, the description that follows generally describes method 1800 in the context of the other figures in this description. However, it will be understood that method 1800 can be performed, for example, by any suitable system, environment, software, and hardware, or a combination of systems, environments, software, and hardware, as appropriate. In some implementations, various steps of method 1800 can be run in parallel, in combination, in loops, or in any order.

At 1802, different boiling curves are received that are calculated for a petroleum sample using different analytical speciation techniques. For example, the different analytical speciation techniques include techniques described in steps 1804, 1806, and 1808.

At 1804, a detailed hydrocarbon analysis (DHA) is used for a speciation of light-end components of the petroleum sample.

At 1806, a comprehensive 2-dimensional (2D) gas chromatography (GCxGC) is used for a speciation of a middle distillates range of the petroleum sample.

At 1808, a high-resolution mass spectrometry is used for a speciation of heavy-end components of the petroleum sample. From 1802, method 1800 proceeds to 1810.

At 1810, a compositional coverage of the different analytical speciation techniques for the petroleum samples is determined using the different boiling curves. Each of the different analytical speciation techniques covers a different boiling range and produces a compositional model modeling a breakdown of components in the petroleum sample by carbon number, aromatic ring family, and heteroatom class. In some implementations, determining the compositional coverage of the different analytical speciation techniques for the petroleum samples can include normalizing and shifting the different boiling curves for the compositional model to match the different boiling curves. For example, matching the different boiling curves can include matching one or more of a true boiling point distillation and simulated distillation. After 1810, method 1800 can stop.

In some implementations, in addition to (or in combination with) any previously-described features, techniques of the present disclosure can include the following. Customized user interfaces can present intermediate or final results of the above described processes to a user. The presented information can be presented in one or more textual, tabular, or graphical formats, such as through a dashboard. The information can be presented at one or more on-site locations (such as at an oil well or other facility), on the Internet (such as on a webpage), on a mobile application (or "app"), or at a central processing facility. For example, outputs of the present disclosure can be used as inputs to other equipment and/or systems at a facility. This can be especially useful for systems or various pieces of equipment that are located several meters or several miles apart, or are located in different countries or other jurisdictions.

Figure 19:
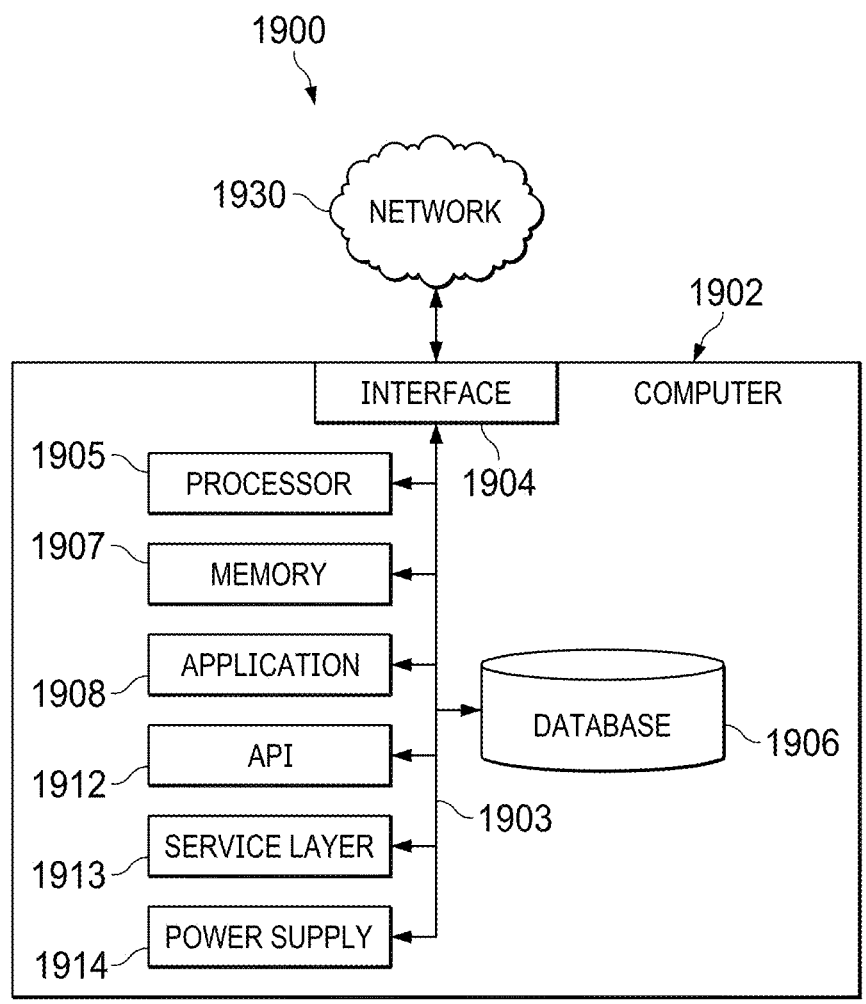
FIG. 19 is a block diagram illustrating an example computer system used to provide computational functionalities associated with described algorithms, methods, functions, processes, flows, and procedures as described in the present disclosure, according to some implementations of the present disclosure.

FIG. 19 is a block diagram of an example computer system 1900 used to provide computational functionalities associated with described algorithms, methods, functions, processes, flows, and procedures described in the present disclosure, according to some implementations of the present disclosure. The illustrated computer 1902 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1902 can include input devices such as keypads, keyboards, and touch screens that can accept user information. Also, the computer 1902 can include output devices that can convey information associated with the operation of the computer 1902. The information can include digital data, visual data, audio information, or a combination of information. The information can be presented in a graphical user interface (UI) (or GUI).

The computer 1902 can serve in a role as a client, a network component, a server, a database, a persistency, or components of a computer system for performing the subject matter described in the present disclosure. The illustrated computer 1902 is communicably coupled with a network

1930. In some implementations, one or more components of the computer 1902 can be configured to operate within different environments, including cloud-computing-based environments, local environments, global environments, and combinations of environments.

At a top level, the computer 1902 is an electronic computing device operable to receive, transmit, process, store, and manage data and information associated with the described subject matter. According to some implementations, the computer 1902 can also include, or be communicably coupled with, an application server, an email server, a web server, a caching server, a streaming data server, or a combination of servers.

The computer 1902 can receive requests over network 1930 from a client application (e.g., executing on another computer 1902). The computer 1902 can respond to the received requests by processing the received requests using software applications. Requests can also be sent to the computer 1902 from internal users (e.g., from a command console), external (or third) parties, automated applications, entities, individuals, systems, and computers.

Each of the components of the computer 1902 can communicate using a system bus 1903. In some implementations, any or all of the components of the computer 1902, including hardware or software components, can interface with each other or the interface 1904 (or a combination of both) over the system bus 1903. Interfaces can use an application programming interface (API) 1912, a service layer 1913, or a combination of the API 1912 and service layer 1913. The API 1912 can include specifications for routines, data structures, and object classes. The API 1912 can be either computer-language independent or dependent. The API 1912 can refer to a complete interface, a single function, or a set of APIs.

The service layer 1913 can provide software services to the computer 1902 and other components (whether illustrated or not) that are communicably coupled to the computer 1902. The functionality of the computer 1902 can be accessible for all service consumers using this service layer. Software services, such as those provided by the service layer 1913, can provide reusable, defined functionalities through a defined interface. For example, the interface can be software written in JAVA, C++, or a language providing data in extensible markup language (XML) format. While illustrated as an integrated component of the computer 1902, in alternative implementations, the API 1912 or the service layer 1913 can be stand-alone components in relation to other components of the computer 1902 and other components communicably coupled to the computer 1902. Moreover, any or all parts of the API 1912 or the service layer 1913 can be implemented as child or sub-modules of another software module, enterprise application, or hardware module without departing from the scope of the present disclosure.

The computer 1902 includes an interface 1904. Although illustrated as a single interface 1904 in FIG. 19, two or more interfaces 1904 can be used according to particular needs, desires, or particular implementations of the computer 1902 and the described functionality. The interface 1904 can be used by the computer 1902 for communicating with other systems that are connected to the network 1930 (whether illustrated or not) in a distributed environment. Generally, the interface 1904 can include, or be implemented using, logic encoded in software or hardware (or a combination of software and hardware) operable to communicate with the network 1930. More specifically, the interface 1904 can include software supporting one or more communication protocols associated with communications. As such, the network 1930 or the interface's hardware can be operable to communicate physical signals within and outside of the illustrated computer 1902.

The computer 1902 includes a processor 1905. Although illustrated as a single processor 1905 in FIG. 19, two or more processors 1905 can be used according to particular needs, desires, or particular implementations of the computer 1902 and the described functionality. Generally, the processor 1905 can execute instructions and can manipulate data to perform the operations of the computer 1902, including operations using algorithms, methods, functions, processes, flows, and procedures as described in the present disclosure.

The computer 1902 also includes a database 1906 that can hold data for the computer 1902 and other components connected to the network 1930 (whether illustrated or not). For example, database 1906 can be an in-memory, conventional, or a database storing data consistent with the present disclosure. In some implementations, database 1906 can be a combination of two or more different database types (e.g., hybrid in-memory and conventional databases) according to particular needs, desires, or particular implementations of the computer 1902 and the described functionality. Although illustrated as a single database 1906 in FIG. 19, two or more databases (of the same, different, or combination of types) can be used according to particular needs, desires, or particular implementations of the computer 1902 and the described functionality. While database 1906 is illustrated as an internal component of the computer 1902, in alternative implementations, database 1906 can be external to the computer 1902.

The computer 1902 also includes a memory 1907 that can hold data for the computer 1902 or a combination of components connected to the network 1930 (whether illustrated or not). Memory 1907 can store any data consistent with the present disclosure. In some implementations, memory 1907 can be a combination of two or more different types of memory (e.g., a combination of semiconductor and magnetic storage) according to particular needs, desires, or particular implementations of the computer 1902 and the described functionality. Although illustrated as a single memory 1907 in FIG. 19, two or more memories 1907 (of the same, different, or combination of types) can be used according to particular needs, desires, or particular implementations of the computer 1902 and the described functionality. While memory 1907 is illustrated as an internal component of the computer 1902, in alternative implementations, memory 1907 can be external to the computer 1902.

The application 1908 can be an algorithmic software engine providing functionality according to particular needs, desires, or particular implementations of the computer 1902 and the described functionality. For example, application 1908 can serve as one or more components, modules, or applications. Further, although illustrated as a single application 1908, the application 1908 can be implemented as multiple applications 1908 on the computer 1902. In addition, although illustrated as internal to the computer 1902, in alternative implementations, the application 1908 can be external to the computer 1902.

The computer 1902 can also include a power supply 1914. The power supply 1914 can include a rechargeable or non-rechargeable battery that can be configured to be either user- or non-user-replaceable. In some implementations, the power supply 1914 can include power-conversion and management circuits, including recharging, standby, and power management functionalities. In some implementations, the power-supply 1914 can include a power plug to allow the computer 1902 to be plugged into a wall socket or a power source to, for example, power the computer 1902 or recharge a rechargeable battery.

There can be any number of computers 1902 associated with, or external to, a computer system containing computer 1902, with each computer 1902 communicating over network 1930. Further, the terms "client," "user," and other appropriate terminology can be used interchangeably, as appropriate, without departing from the scope of the present disclosure. Moreover, the present disclosure contemplates that many users can use one computer 1902 and one user can use multiple computers 1902.

Described implementations of the subject matter can include one or more features, alone or in combination.

For example, in a first implementation, a computer-implemented method includes the following. Different boiling curves are received that are calculated for a petroleum sample using different analytical speciation techniques. The boiling curves include: 1) a detailed hydrocarbon analysis (DHA) is used for a speciation of light-end components of the petroleum sample; 2) a comprehensive 2-dimensional (2D) gas chromatography (GCxGC) is used for a speciation of a middle distillates range of the petroleum sample; and 3) a high-resolution mass spectrometry is used for a speciation of heavy-end components of the petroleum sample. A compositional coverage of the different analytical speciation techniques for the petroleum samples is determined using the different boiling curves. Each of the different analytical speciation techniques covers a different boiling range and produces a compositional model modeling a breakdown of components in the petroleum sample by carbon number, aromatic ring family, and heteroatom class.

The foregoing and other described implementations can each, optionally, include one or more of the following features:

A first feature, combinable with any of the following features, where determining the compositional coverage of the different analytical speciation techniques for the petroleum samples includes normalizing and shifting the different boiling curves for the compositional model to match the different boiling curves.

A second feature, combinable with any of the previous or following features, where matching the different boiling curves with one or more of a true boiling point distillation and simulated distillation curves.

A third feature, combinable with any of the previous or following features, where the model captures molecular details, including chemical and boiling information listed for each component, including, for each component family, number of aromatic rings (AR #), number of carbon atoms (C #), DBE value, mass fractions (MF) of the component, atmospheric equivalent boiling point (AEBP), and the cumulative mass fraction (cMF).

A fourth feature, combinable with any of the previous or following features, the method further including generating a bar graph plotting composition data by compound family, including hydrocarbon compounds, sulfur containing compounds.

A fifth feature, combinable with any of the previous or following features, the method further including generating a bar graph plotting a carbon number breakdown for the individual compound families, plotted relative to a mass fraction.

A sixth feature, combinable with any of the previous or following features, where bars in the bar graph are labeled with a three-part compound identifier including a compound type, a number of aromatic rings, and a number of naphthenic rings for saturated compounds, wherein the compound type includes saturated compounds, aromatic hydrocarbon compounds, and sulfur containing compounds.

In a second implementation, a non-transitory, computer-readable medium stores one or more instructions executable by a computer system to perform operations including the following. Different boiling curves are received that are calculated for a petroleum sample using different analytical speciation techniques. The boiling curves include: 1) a detailed hydrocarbon analysis (DHA) is used for a speciation of light-end components of the petroleum sample; 2) a comprehensive 2-dimensional (2D) gas chromatography (GCxGC) is used for a speciation of a middle distillates range of the petroleum sample; and 3) a high-resolution mass spectrometry is used for a speciation of heavy-end components of the petroleum sample. A compositional coverage of the different analytical speciation techniques for the petroleum samples is determined using the different boiling curves. Each of the different analytical speciation techniques covers a different boiling range and produces a compositional model modeling a breakdown of components in the petroleum sample by carbon number, aromatic ring family, and heteroatom class.

The foregoing and other described implementations can each, optionally, include one or more of the following features:

A first feature, combinable with any of the following features, where determining the compositional coverage of the different analytical speciation techniques for the petroleum samples includes normalizing and shifting the different boiling curves for the compositional model to match the different boiling curves.

A second feature, combinable with any of the previous or following features, where matching the different boiling curves with one or more of a true boiling point distillation and simulated distillation curves.

A third feature, combinable with any of the previous or following features, where the model captures molecular details, including chemical and boiling information listed for each component, including, for each component family, number of aromatic rings (AR #), number of carbon atoms (C #), DBE value, mass fractions (MF) of the component, atmospheric equivalent boiling point (AEBP), and the cumulative mass fraction (cMF).

A fourth feature, combinable with any of the previous or following features, the operations further including generating a bar graph plotting composition data by compound family, including hydrocarbon compounds, sulfur containing compounds.

A fifth feature, combinable with any of the previous or following features, the operations further including generating a bar graph plotting a carbon number breakdown for the individual compound families, plotted relative to a mass fraction.

A sixth feature, combinable with any of the previous or following features, where bars in the bar graph are labeled with a three-part compound identifier including a compound type, a number of aromatic rings, and a number of naphthenic rings for saturated compounds, wherein the compound type includes saturated compounds, aromatic hydrocarbon compounds, and sulfur containing compounds.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. Different boiling curves are received that are calculated for a petroleum sample using different analytical speciation techniques. The boiling curves include: 1) a detailed hydrocarbon analysis (DHA) is used for a speciation of light-end components of the petroleum sample; 2) a comprehensive 2-dimensional (2D) gas chromatography (GCxGC) is used for a speciation of a middle distillates range of the petroleum sample; and 3) a high-resolution mass spectrometry is used for a speciation of heavy-end components of the petroleum sample. A compositional coverage of the different analytical speciation techniques for the petroleum samples is determined using the different boiling curves. Each of the different analytical speciation techniques covers a different boiling range and produces a compositional model modeling a breakdown of components in the petroleum sample by carbon number, aromatic ring family, and heteroatom class.

The foregoing and other described implementations can each, optionally, include one or more of the following features:

A first feature, combinable with any of the following features, where determining the compositional coverage of the different analytical speciation techniques for the petroleum samples includes normalizing and shifting the different boiling curves for the compositional model to match the different boiling curves.

A second feature, combinable with any of the previous or following features, where matching the different boiling curves with one or more of a true boiling point distillation and simulated distillation curves.

A third feature, combinable with any of the previous or following features, where the model captures molecular details, including chemical and boiling information listed for each component, including, for each component family, number of aromatic rings (AR #), number of carbon atoms (C #), DBE value, mass fractions (MF) of the component, atmospheric equivalent boiling point (AEBP), and the cumulative mass fraction (cMF).

A fourth feature, combinable with any of the previous or following features, the operations further including generating a bar graph plotting composition data by compound family, including hydrocarbon compounds, sulfur containing compounds.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (e.g., using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method for petroleum sample analysis, comprising:
    executing a detailed hydrocarbon analysis (DHA) for a speciation of light-end components of a first boiling curve of a petroleum sample having a volume of approximately one milliliter, obtained from an unfractionated sample;
    executing a comprehensive 2-dimensional (2D) gas chromatography (GCxGC) for a speciation of a middle distillates range of a second boiling curve of the petroleum sample;
    executing a high-resolution mass spectrometry for a speciation of heavy-end components of a third boiling curve of the petroleum sample; and
    determining, using different boiling curves comprising the first boiling curve, the second boiling curve, and the third boiling curve, a compositional coverage of different analytical speciation techniques for the petroleum sample, wherein the different analytical speciation techniques comprise the DHA, the 2D GCxGC, and the high-resolution mass spectrometry, each of the different analytical speciation techniques covers a different boiling range and produces a compositional model modeling breakdown of components in the petroleum sample by carbon number, aromatic ring family, and a heteroatom class.

2. The computer-implemented method of claim 1, wherein determining the compositional coverage of the different analytical speciation techniques for the petroleum sample comprises normalizing and shifting the different boiling curves for the compositional model to match the different boiling curves.

3. The computer-implemented method of claim 2, wherein matching the different boiling curves with one or more of a true boiling point distillation and simulated distillation curves.

4. The computer-implemented method of claim 1, wherein the compositional model captures molecular details, comprising chemical and boiling information listed for each component, comprising, for each component family, number of aromatic rings (AR #), number of carbon atoms (C #), DBE value, mass fractions (MF) of the component, atmospheric equivalent boiling point (AEBP), and a cumulative mass fraction (cMF).

5. The computer-implemented method of claim 1, further comprising generating a bar graph plotting composition data by compound family, comprising hydrocarbon compounds, sulfur containing compounds.

6. The computer-implemented method of claim 1, further comprising generating a bar graph plotting a carbon number breakdown for individual compound families, plotted relative to a mass fraction.

7. The computer-implemented method of claim 6, wherein bars in the bar graph are labeled with a three-part compound identifier comprising a compound type, a number of aromatic rings, and a number of naphthenic rings for saturated compounds, wherein the compound type comprises saturated compounds, aromatic hydrocarbon compounds, and sulfur containing compounds.

8. A non-transitory, computer-readable medium storing one or more instructions executable by a computer system to perform operations comprising:
    executing a detailed hydrocarbon analysis (DHA) for a speciation of light-end components of a first boiling curve of a petroleum sample having a volume of approximately one milliliter, obtained from an unfractionated sample;
    executing a comprehensive 2-dimensional (2D) gas chromatography (GCxGC) for a speciation of a middle distillates range of a second boiling curve of the petroleum sample;
    executing a high-resolution mass spectrometry for a speciation of heavy-end components of a third boiling curve of the petroleum sample; and
    determining, using different boiling curves comprising the first boiling curve, the second boiling curve, and the third boiling curve, a compositional coverage of different analytical speciation techniques for the petroleum sample, wherein the different analytical speciation techniques comprise the DHA, the 2D GCxGC, and the high-resolution mass spectrometry, each of the different analytical speciation techniques covers a different boiling range and produces a compositional model modeling breakdown of components in the petroleum sample by carbon number, aromatic ring family, and a heteroatom class.

9. The non-transitory, computer-readable medium of claim 8, wherein determining the compositional coverage of the different analytical speciation techniques for the petroleum sample comprises normalizing and shifting the different boiling curves for the compositional model to match the different boiling curves.

10. The non-transitory, computer-readable medium of claim 9, wherein matching the different boiling curves with one or more of a true boiling point distillation and simulated distillation curves.

11. The non-transitory, computer-readable medium of claim 8, wherein the compositional model captures molecular details, comprising chemical and boiling information listed for each component, comprising, for each component family, number of aromatic rings (AR #), number of carbon atoms (C #), DBE value, mass fractions (MF) of the component, atmospheric equivalent boiling point (AEBP), and a cumulative mass fraction (cMF).

12. The non-transitory, computer-readable medium of claim 8, the operations further comprising generating a bar graph plotting composition data by compound family, comprising hydrocarbon compounds, sulfur containing compounds.

13. The non-transitory, computer-readable medium of claim 8, the operations further comprising generating a bar graph plotting a carbon number breakdown for individual compound families, plotted relative to a mass fraction.

14. The non-transitory, computer-readable medium of claim 13, wherein bars in the bar graph are labeled with a three-part compound identifier comprising a compound type, a number of aromatic rings, and a number of naphthenic rings for saturated compounds, wherein the compound type comprises saturated compounds, aromatic hydrocarbon compounds, and sulfur containing compounds.

15. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:
executing a detailed hydrocarbon analysis (DHA) for a speciation of light-end components of a first boiling curve of a petroleum sample having a volume of approximately one milliliter, obtained from an unfractionated sample;
executing a comprehensive 2-dimensional (2D) gas chromatography (GCxGC) for a speciation of a middle distillates range of a second boiling curve of the petroleum sample;
executing a high-resolution mass spectrometry for a speciation of heavy-end components of a third boiling curve of the petroleum sample; and
determining, using different boiling curves comprising the first boiling curve, the second boiling curve, and the third boiling curve, a compositional coverage of different analytical speciation techniques for the petroleum sample, wherein the different analytical speciation techniques comprise the DHA, the 2D GCxGC, and the high-resolution mass spectrometry, each of the different analytical speciation techniques covers a different boiling range and produces a compositional model modeling breakdown of components in the petroleum sample by carbon number, aromatic ring family, and a heteroatom class.

16. The computer-implemented system of claim 15, wherein determining the compositional coverage of the different analytical speciation techniques for the petroleum sample comprises normalizing and shifting the different boiling curves for the compositional model to match the different boiling curves.

17. The computer-implemented system of claim 16, wherein matching the different boiling curves with one or more of a true boiling point distillation and simulated distillation curves.

18. The computer-implemented system of claim 15, wherein the compositional model captures molecular details, comprising chemical and boiling information listed for each component, comprising, for each component family, number of aromatic rings (AR #), number of carbon atoms (C #), DBE value, mass fractions (MF) of the component, atmospheric equivalent boiling point (AEBP), and a cumulative mass fraction (cMF).

19. The computer-implemented system of claim 15, the operations further comprising generating a bar graph plotting composition data by compound family, comprising hydrocarbon compounds, sulfur containing compounds.

20. The computer-implemented system of claim 15, the operations further comprising generating a bar graph plotting a carbon number breakdown for individual compound families, plotted relative to a mass fraction.

\* \* \* \* \*